US010890532B2

(12) United States Patent
Recht et al.

(10) Patent No.: US 10,890,532 B2
(45) Date of Patent: Jan. 12, 2021

(54) COMPOSITIONS AND METHODS FOR PERFORMING ASSAYS

(71) Applicant: Palo Alto Research Center Incorporated, Palo Alto, CA (US)

(72) Inventors: Michael I. Recht, Mountain View, CA (US); Peter Kiesel, Palo Alto, CA (US); Joerg Martini, San Francisco, CA (US); Francisco E. Torres, San Jose, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 253 days.

(21) Appl. No.: 15/657,607

(22) Filed: Jul. 24, 2017

(65) Prior Publication Data
US 2017/0322160 A1 Nov. 9, 2017

Related U.S. Application Data

(62) Division of application No. 13/826,198, filed on Mar. 14, 2013, now abandoned.

(51) Int. Cl.
G01N 21/64 (2006.01)
C12Q 1/00 (2006.01)
G01N 33/58 (2006.01)

(52) U.S. Cl.
CPC ........... *G01N 21/6486* (2013.01); *C12Q 1/00* (2013.01); *G01N 33/582* (2013.01); *G01N 2333/90209* (2013.01)

(58) Field of Classification Search
CPC ................ C12Q 1/00; G01N 21/6486; G01N 2333/90209; G01N 33/582
See application file for complete search history.

(56) References Cited

U.S. PATENT DOCUMENTS

| | | | |
|---|---|---|---|
| 4,557,862 A | 12/1985 | Mangel et al. | |
| 4,640,893 A | 2/1987 | Mangel et al. | |
| 7,527,934 B2 | 5/2009 | Ying et al. | |
| 7,534,902 B2 | 5/2009 | Raines et al. | |
| 8,153,811 B2 | 4/2012 | Huang et al. | |
| 2006/0057658 A1 | 3/2006 | Ying et al. | |
| 2008/0181827 A1* | 7/2008 | Bassler ................ | G01N 15/147 422/119 |
| 2009/0004753 A1 | 1/2009 | Antoulinakis et al. | |
| 2010/0047839 A1 | 2/2010 | Huang et al. | |

OTHER PUBLICATIONS

Ren et al., "A biocompatible condensation reaction for the labeling of terminal cysteine residues on proteins," Angew. Chem., Int. Ed., 2009, vol. 48, pp. 9658-9662.*
Kim et al., "Utilization of microparticles in next-generation assays for microflow cytometers," Anal. Bioanal. Chem., 2010, vol. 398, pp. 2373-2382.*
Sperling et al., "Surface modification, functionalization and bioconjugation of colloidal inorganic nanoparticles," Phil. Trans. R. Soc., 2010, vol. 368, pp. 1333-1383.
Biomarin Pharmaceutical Inc. (BMRN) Apr. 2011 Earnings Call Feb. 16, 2012 5:00AM ET. Jun. 1, 2012, 1 2012; Available from: http://seekingalpha.com/article/373831-biomarin-pharmaceutical-s-ceo-discusses-q4-2011- Dearning-results-earnings-call-transcript.
Chandran, S.S., et al., "Latent Fluorophore Based on the Trimethyl Lock," Journal of the American Chemical Society, 2005, 127(6), pp. 1652-1653.
Cooper, A.J., et al., "Enzymatic Cycling Assay for Phenylpyruvate," Analytical Biochemistry, 1989, 183(2), pp. 210-214.
De Silva, V., et al., "L-Phenylalanine Concentration in Blood of Phenylketonuria Patients: A Modified Enzyme Colorimetric Assay Compared with Amino Acid Analysis, Tandem Mass Spectrometry, and HPLC Methods," Clinical Chemistry and Laboratory Medicine: CCLM/FESCC, 2010, 48(9), pp. 1271-1279.
Huang, T., et al., "Determination of L-phenylalanine Based on a NADH-detecting Biosensor," Analytical Chemistry, 1998, 70(5), pp. 991-997.
Huang. S.T., et al., "New Latent Fluorophore for DT Diaphorase," Organic Letters, 2006, 8(2), pp. 265-268.
Huang, S.T., et al., "Synthesis of a New Long-Wavelength Latent Fluorimetric Indicator for Analytes Determination in the DT-Diaphorase Coupling Dehydrogenase Assay System," Biosensors & Bioelectronics, 2008, 23(12), pp. 1793-1798.
Hummel, W., et al., "Enzymatic Determination of L-phenylalanine and Phenylpyruvate with L-phenylalanine Dehydrogenase," Analytical Biochemistry, 1988, 170(2), pp. 397-401.
Kiesel, P., et al., "Flow Cytometry on a Chip, in Point-of-Care Diagnostics on a Chip," D. Issadore and R. Westervelt, Editors 2012; in press, Springer.
Kiesel, P., et al., "Spatially Modulated Fluorescence Emission From Moving Particles," Applied Physics Letters, 2009, 94(4), pp. 041107-3.
Lavis, L.D., et al., "Fiuorogenic Label for Biomolecular Imaging," ACS Chemical Biology, 2006, 1(4), pp. 252-260.
Levine, M. N., et al., "Sensitive Fluorogenic Substrate for Alkaline Phosphatase," Analytical Biochemistry, (2012), 418, pp. 247-252.
Levine, M. N., et al., "Trimethyl Lock: A Stable Chromogenic Substrate for Esterases," Molecules 13, 2008, ISSN 1420-3049, pp. 204-211.
Leytus, S. P., et al., "Rhodamine-based Compounds as Fluorogenic Substrates for Serine Proteinases," Biochem. J, (1983) 209, pp. 299-307.

(Continued)

Primary Examiner — Galina M. Yakovleva
(74) Attorney, Agent, or Firm — The Marbury Law Group, PLLC

(57) ABSTRACT

The disclosure relates to compositions for use in assays, the compositions comprising at least one latent fluorophore including at least one enzyme-reactive quenching group and a conjugative group; and a support connectable to the latent fluorophore by the conjugative group. The disclosure further relates to methods of measuring the presence and/or concentration of an analyte, as well as methods of measuring the relative activity of at least two enzymes.

8 Claims, 14 Drawing Sheets

(56) References Cited

OTHER PUBLICATIONS

Richens, J.L., et al., "Quantitative Validation and Comparison of Multiplex Cytokine Kits," Journal of Biomolecular Screening, 2010, 15(5), pp. 562-568.
Sourial. S .. et al., "Meso Scale Discovery and Luminex Comparative Analysis of Calbindin D28K," Journal of Biomedicine & Biotechnology, 2009, pp. 187426.
Watkins, R.W., et al., "Fiuorogenic Affinity Label for the Facile, Rapid Imagining of Proteins in Live Cells," Organic & Biomolecular Chemistry, 2009, 7(19), pp. 3969-3975.
Wendel, U., et al., "Monitoring of Phenylketonuria: A Colorimetric Method for the Determination of Plasma Phenylalanine Using L-phenylalanine Dehydrogenase," Analytical Biochemistry, 1989, 180(1), pp. 91-94.
Wibrand, F., "A Microplate-Based Enzymatic Assay for the Simultaneous Determination of Phenylalanine and Tyrosin in Serum," Clinica Chimica Acta; International Journal of Clinical Chemistry, 2004, 347(1-2), pp. 89-96.
Zlokarnik, G., et al., "Quantitation of Transcription and Clonal Selection of Single Living Cells with Beta-Lactamase as Reporter," Science, 1998, 279(5347), pp. 84-88.
Kofoed, K., et al., "Development and Validation of a Multiplex Add-on Assay for Sepsis Biomarkers Using xMAP Technology," Clinical Chemistry, 2006, 52(7), pp. 1284-1293.

* cited by examiner

COMPOSITIONS AND METHODS FOR PERFORMING ASSAYS

CROSS REFERENCE TO RELATED APPLICATION

This is a divisional of U.S. application Ser. No. 13/826,198, filed on Mar. 14, 2013, which is incorporated herein by reference in its entirety.

STATEMENT REGARDING FEDERALLY SPONSORED RESEARCH AND DEVELOPMENT

This invention was made with government support under 1R21EB011662-01 awarded by the National Institutes of Health. The government has certain rights in the invention.

TECHNICAL FIELD

The present disclosure relates to compositions and methods for performing assays. In various embodiments, the disclosure relates to latent fluorophores linked to a support, and their use in assays.

BACKGROUND

Assays are commonly used for qualitatively assessing or quantitatively measuring the presence, amount, or functional activity of a target entity (the analyte). The analyte may, in various assays, be a drug, biochemical substance, or biological cell. By way of example, certain medical conditions may utilize an assay to screen for the presence of a target entity, or measure the amount of the target entity, in bodily fluids such as urine, saliva, or blood.

For example, phenylketonuria (PKU) is a genetic condition characterized by the inability to metabolize the amino acid phenylalanine. As a result, individuals exhibiting this condition must control their intake of phenylalanine, and some use blood tests (assays) to monitor the amount of phenylalanine (the analyte) in their blood serum. Likewise, blood serum levels of phenylalanine may be used to screen for, or diagnose, PKU.

Methods for laboratory quantitation of phenylalanine levels in serum include a variety of enzyme assays having colorimetric or fluorescence signals. For example, latent fluorophores are compounds with intense fluorescence that is revealed by a user-designated chemical reaction. Latent fluorophores using a trimethyl lock mechanism to cloak or quench fluorescence can be used to detect levels of phenylalanine by coupling the reaction of phenylalanine dehydrogenase to a diaphorase-activated trimethyl lock quenched latent fluorophore. The fluorescence intensity of the sample may be substantially directly proportional to the amount of phenylalanine present. This technique can provide a broad dynamic range, but requires several blood sample processing steps to improve the signal-to-noise ratio, such as isolating the serum from whole blood and deproteinizing the serum.

The above-mentioned processing steps require equipment and techniques that are not ideal for adaptation to at-home testing devices. At-home phenylalanine testing devices are desirable though, as they may allow for more frequent and convenient monitoring of blood phenylalanine levels.

There is, therefore, a need for at-home phenylalanine testing devices capable of testing whole blood, and capable of supplying a measurement signal having a broad dynamic range and a high signal-to-noise ratio. Accordingly, there is a need for assays that may be useful in such at-home devices, compositions for use in the assays, and methods of measuring the concentration of an analyte, such as phenylalanine, in a sample, such as whole blood. More generally, there is a need for compositions and methods of detecting and/or measuring an analyte in a sample.

SUMMARY

The disclosure relates, in various embodiments, to compositions for use in assays. The compositions may, in various exemplary embodiments, comprise at least one latent fluorophore comprising at least one enzyme-reactive quenching group and at least one conjugative group; and a support connectable to the latent fluorophore, for example by at least one conjugative group.

Further embodiments of the disclosure relate to methods for measuring the concentration and/or presence of an analyte in a sample. In various exemplary embodiments, the methods comprise one or more steps chosen from:
a. providing a fluorophore composition comprising:
   i. at least one enzyme-reactive latent fluorophore comprising at least one enzyme-reactive quenching group and at least one conjugative group, and
   ii. a support connectable to the latent fluorophore by at least one conjugative group;
b. providing a test sample to be analyzed and a reference sample to be analyzed;
c. contacting the test sample with the latent fluorophore composition, at least one first unquenching enzyme capable of releasing the enzyme-reactive quenching group from the latent fluorophore, and at least one second enzyme capable of reacting with the analyte;
d. contacting the reference sample with the latent fluorophore composition and the at least one first unquenching enzyme;
e. measuring the fluorescence signal of the test sample and the fluorescence signal of the reference sample; and
f. comparing the fluorescence signal of the test sample with the fluorescence signal of the reference sample.

Further embodiments of the disclosure relate to methods for measuring the activity and/or presence of an enzyme in a test sample including an analyte. In various exemplary embodiments, the methods comprise one or more steps chosen from:
a. providing a fluorophore composition comprising:
   i. at least one enzyme-reactive latent fluorophore comprising at least one enzyme-reactive quenching group and at least one conjugative group, and
   ii. a support connectable to the latent fluorophore by at least one conjugative group;
b. providing a test sample to be analyzed and a reference sample to be analyzed, wherein the reference sample contains a known quantity of the analyte;
c. contacting the test sample with the latent fluorophore composition, at least one first unquenching enzyme capable of releasing the enzyme-reactive quenching group from the latent fluorophore, and at least one second enzyme capable of reacting with the analyte;
d. contacting the reference sample with the latent fluorophore composition and the at least one first unquenching enzyme;
e. measuring the fluorescence signal of the test sample and the fluorescence signal of the reference sample; and
f. comparing the fluorescence signal of the test sample with the fluorescence signal of the reference sample.

Further exemplary embodiments of the disclosure relate to methods for measuring the activities of at least two enzymes in a sample, for example a multiplexed assay. In various embodiments, the methods comprise one or more steps chosen from:

a. providing a first fluorophore composition comprising:
  i. at least one first enzyme-reactive latent fluorophore including at least one first enzyme-reactive quenching group and at least one conjugative group, and
  ii. at least one support connectable to the at least one first latent fluorophore by at least one conjugative group;
b. providing a second fluorophore composition comprising:
  i. at least one second enzyme-reactive latent fluorophore including at least one second enzyme-reactive quenching group and at least one conjugative group, wherein the at least one second enzyme-reactive latent fluorophore is different from said first enzyme-reactive latent fluorophore in said first fluorophore composition, and
  ii. at least one support connectable to the at least one first latent fluorophore by at least one conjugative group;
c. providing a test sample to be analyzed and a reference sample to be analyzed;
d. contacting the test sample with the first and second latent fluorophore compositions, at least one first unquenching enzyme capable of releasing the enzyme-reactive quenching group from the first latent fluorophore, and at least one second unquenching enzyme capable of releasing the enzyme-reactive quenching group from the second latent fluorophore;
e. contacting the reference sample with the first and second latent fluorophore compositions;
f. measuring the fluorescence signals of the test sample and the fluorescence signals of the reference sample; and
g. comparing the fluorescence signals of the test sample with the fluorescence signals of the reference sample.

Yet a further exemplary embodiment of the disclosure relates to a kit comprising a composition, where the composition comprises at least one latent fluorophore comprising at least one enzyme-reactive quenching group and at least one conjugative group, and at least one support connectible to the at least one latent fluorophore via at least one conjugative group.

Additional objects and advantages will be set forth in part in the description which follows, and in part will be obvious from the description, or may be learned by practice of various embodiments according to the disclosure.

It is to be understood that both the foregoing general description and the following detailed description are exemplary and explanatory only, and are not restrictive of the invention, as claimed.

The accompanying figures, which are incorporated in and constitute a part of this specification, illustrate several exemplary embodiments of the disclosure and, together with the description, serve to explain the principles of the disclosure.

DESCRIPTION OF EXEMPLARY EMBODIMENTS

Figure 1:
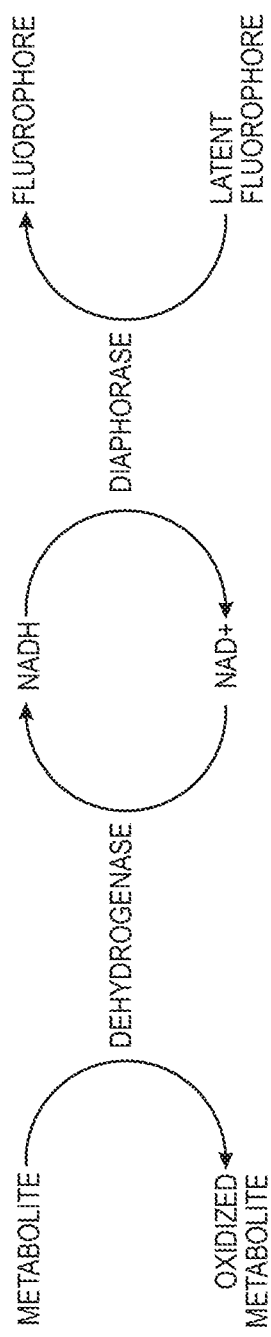
FIG. 1 is an exemplary schematic of a coupled assay for detecting an analyte having a specific dehydrogenase according to an embodiment of the disclosure.

The disclosure relates, in various exemplary embodiments, to compositions for use in an assay. In various exemplary embodiments, the measurement from the assay is used to detect levels of phenylalanine in whole blood.

In various exemplary embodiments, the compositions comprise at least one latent fluorophore and at least one support. In further exemplary embodiments, the composition is an enzyme-reactive latent fluorophore cloaked or quenched by an enzyme-reactive group, and the latent fluorophore is linked to the support. In at least certain exemplary embodiments, the enzyme-reactive quenching group may be released by a trimethyl lock mechanism, and the enzyme-reactive latent fluorophore may be revealed or unquenched by an enzymatic reaction. The resulting fluorescence intensity of the sample may, in certain embodiments, be proportional to the amount of enzyme activity. In various embodiments, the support may be chosen from microspheres, microbeads, or beads.

In various exemplary embodiments, the assay using the composition comprising the at least one latent fluorophore and at least one support may exhibit a broad dynamic range and high signal-to-noise ratio, although it should be noted that a broad dynamic range and high signal-to-noise ratio are not required.

In at least certain embodiments, the latent fluorophore is attached to the support with a linking group. By way of non-limiting example, the linker may be chosen from poly-ethylene glycol ("PEG") linkers. In certain embodiments, the latent fluorophore is attached to the support with at least one conjugate. In at least one embodiment, the conjugate may be biotin, and the support may be coated with a suitable complementary functional group, for example streptavidin.

According to various embodiments of the disclosure, compositions comprising the latent fluorophore may be contacted with at least one enzyme. In various exemplary embodiments, the latent fluorophore is attached to the support prior to the enzymatic reaction; in other exemplary embodiments, it is attached after the enzymatic reaction.

In at least certain embodiments according to the disclosure, the fluorescence of the composition used in the analyte assay can be determined by measuring bulk fluorescence. In various embodiments, the fluorescence is measured using flow cytometry or spatially modulated fluorescence detection technology. However, it should be noted that any method of measuring fluorescence known to those skilled in the art may be used according to various embodiments of the disclosure.

Latent Fluorophores

As used herein, the term "latent fluorophore," and variations thereof, means a chemical compound capable of exhibiting fluorescence, which may be revealed by a designated chemical reaction. As used herein, the terms "quench," "quenched," and variations thereof mean a suppression or concealment of some, all, or substantially all fluorescence of a fluorophore by one or more functional groups, referred to herein as "quenching groups." In its quenched state, a latent fluorophore exhibits no or substantially no fluorescence, or a decreased amount of fluorescence compared to its unquenched state.

The quenching group may quench or partially quench a latent fluorophore by various chemical or physical means. In certain embodiments, the quenching group completes a system of conjugated double bonds when altered and/or released from the latent fluorophore, thus allowing fluorescence. The quenching group may be altered and/or released from the latent fluorophore by various chemical or physical means. In certain embodiments, for example, the quenching group may be altered and/or released from the latent fluorophore by a predetermined chemical reaction. In further exemplary embodiments, the predetermined chemical reaction may be catalyzed by an enzyme and/or an enzyme cascade. Nonlimiting examples of enzymes capable of catalyzing the unquenching or unlocking of a latent fluorophore include diaphorase and pyruvate oxidase.

Among the latent fluorophores that may be used according to exemplary embodiments of the disclosure include, but are not limited to, fluorophores quenched by a quenching group releasable by a trimethyl lock mechanism (trimethyl lock fluorophores), and fluorophores quenched by an enzyme-activated trimethyl lock mechanism, such as diaphorase-activated trimethyl lock fluorophores.

Latent fluorophores that may be revealed, unquenched, or unlocked by an enzymatic reaction, referred to herein as "enzyme-reactive latent fluorophores," comprise an enzyme-reactive quenching group that may be altered and/or released from the latent fluorophore upon reaction with or in the presence of the unquenching enzyme. In certain embodiments, the enzyme-reactive quenching group is a trimethyl lock. The resulting fluorophore, an active fluorophore, exhibits fluorescence. Because the alteration and/or release of the enzyme-reactive group is typically irreversible, for example due to the relative thermodynamic stability of the unreacted and reacted quenching group, the fluorescence signal typically remains throughout any subsequent assay steps such as collection, rinsing, and measurement.

According to various exemplary embodiments of the disclosure, fluorophores may be chosen to have certain specific excitation and emission properties. By way of example, the fluorophore may be chosen from fluoresceins and rhodamines. In certain embodiments, the fluorophore may optionally include amine groups on either side of the fluorophore.

The enzyme reactive group may be any moiety having sensitivity and/or specificity toward an unquenching enzyme. In certain exemplary embodiments, the enzyme reactive quenching group activates a trimethyl lock mechanism and is then released from the enzyme-reactive latent fluorophore. A trimethyl lock is a functional group including three methyl groups in close proximity. Steric interactions between these three methyl groups promote a lactone reaction and liberation of a leaving group. The resulting cyclic hydrocoumarin group is thermodynamically favored, making the trimethyl lock mechanism well suited as a fluorophore quenching group. In various embodiments, the unquenching enzyme reacts directly with the trimethyl lock to cleave the enzyme reactive group from the enzyme-reactive latent fluorophore.

Exemplary and non-limiting trimethyl lock fluorophores useful in various embodiments may be chosen from, for example, compounds represented by Chemical Formula 1, Chemical Formula 2, Chemical Formula 3, and mixtures thereof:

Chemical Formula 1

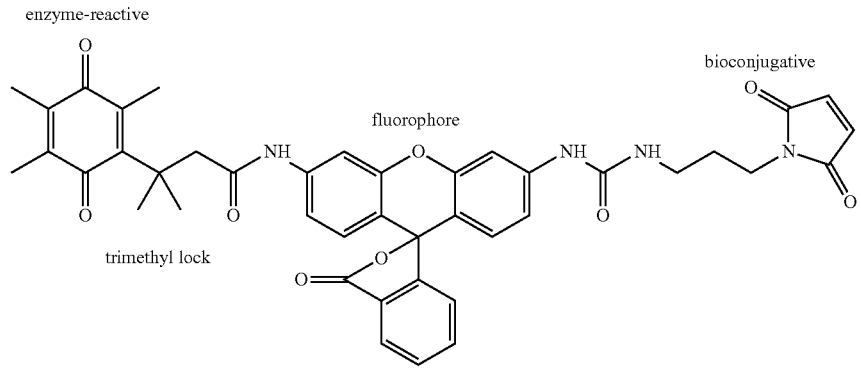

-continued

Chemical Formula 2

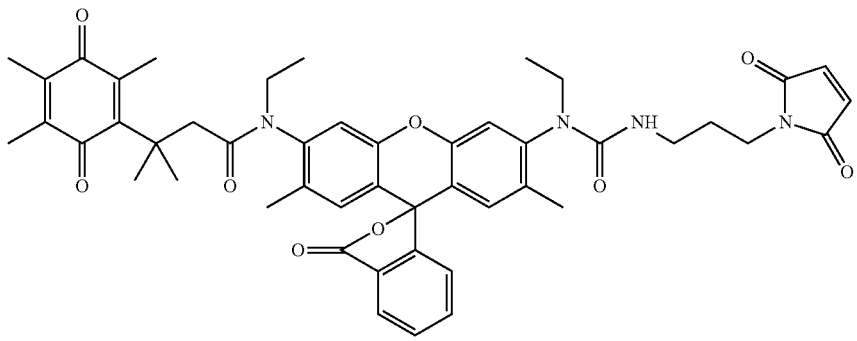

Chemical Formula 3

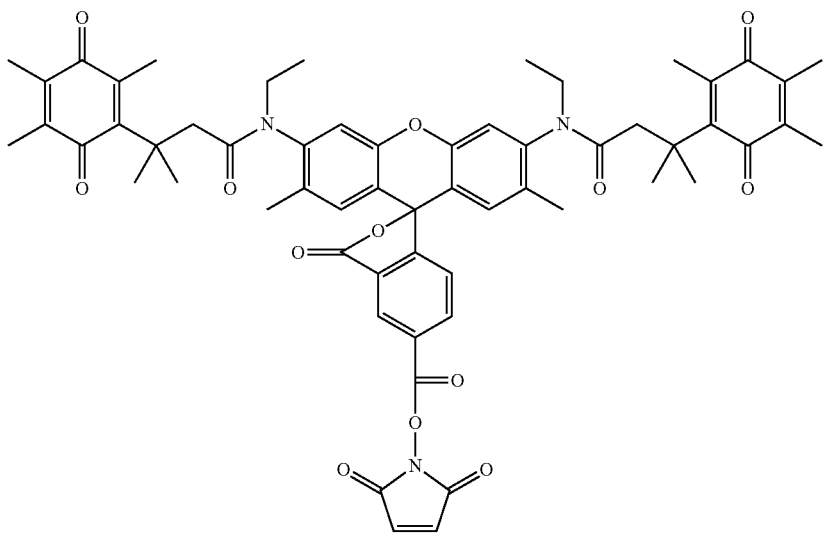

According to various exemplary embodiments of the disclosure, a latent fluorophore quenched by more than one enzyme-reactive quenching group, for example the compound represented by Chemical Formula 3, may be chosen, for example to increase the difference in fluorescence intensity. By way of non-limiting example, in an embodiment where a compound represented by Chemical Formula 3 is chosen, the enzyme-reactive latent fluorophore is quenched by two enzyme-reactive groups. In that exemplary embodiment, the compound fluoresces at a first level of intensity when the first enzyme-reactive group is released, and fluoresces at a higher level of intensity when the second enzyme-reactive group is released.

In various exemplary embodiments, more than one quenching group may be chosen, where different quenching groups have different properties, for example the ability to be altered and/or released by reaction with certain enzymes, rates of reaction, and conditions for reaction. In certain embodiments, multiple latent fluorophores having different quenching groups, and thus having different properties, may be chosen for use in multiplexed assays. In certain embodiments involving different quenching groups, different unlocking enzymes and/or varying reaction conditions may optionally be used.

Conjugative Group

According to various embodiments of the disclosure, the latent fluorophores may be connected to a support by at least one linking group, or conjugative group. As used herein, the terms "connected," "connection," and variations thereof, mean being held in a set or predetermined spatial relationship, or a set or predetermined spatial relationship, and the term "connectable" and variations thereof means capable of being held in a set or predetermined spatial relationship. As used herein, the terms "linking group," "linker," "conjugative group," "bioconjugative group," and variations thereof, which may be used interchangeably, mean a functional group or agent capable, by itself or in the presence of a complementary group, of forming a connection between the latent fluorophore and the support.

In one embodiment, the linking group is a bioconjugative group comprising a pyrrole-2,5-dione group.

It may, in various embodiments, be desirable to choose a conjugate that has a complementary functional group to which it is attracted. By way of non-limiting example, according to one embodiment of the disclosure, the linking group may be chosen from a biotin group or biotin-containing compound. It is known that the biotin group preferentially binds to the protein streptavidin to form a strong protein-ligand interaction, which may be desirable according to certain embodiments of the disclosure. For example, a latent fluorophore containing a biotin linking group will form a connection with a support coated with streptavidin.

According to various embodiments of the disclosure, the linking group may include a polymer or oligomer having a degree of polymerization or polymerization number, n, which indicates the number of repeated monomer units. The polymerization number may determine the length of the polymer or oligomer linker. The polymer or oligomer linker can be of any appropriate length to allow an enzyme to bind the enzyme-reactive quenching group on the enzyme-reactive latent fluorophore by providing a suitable space between the enzyme reactive group and the support. If n is too large, the polymer or oligomer linker will be too long, and may be prone to breakage or other instability. Also, if the polymer or oligomer linker is too long, the fluorophore may form undesirable aggregates. If the polymer or oligomer linker is too short, it may be difficult for the enzyme to access the reactive group. The length of the polymer or oligomer linker can be adjusted so that the enzyme reactive group is accessible to the enzyme.

Thus, in various embodiments, n is any positive number. By way of example, n may range up to about 200, such as up to about 150, up to about 100, up to about 75, up to about 50, up to about 25, or up to about 20, such as about 1 to about 100, about 1 to about 25, about 1 to about 20, about 3 to about 100, about 4 to about 100, about 3 to about 25, about 4 to about 25, or about 4 to about 20. For example, in at least certain non-limiting embodiments, n ranges from about 1 to about 25. In yet further exemplary embodiments, n ranges from about 3 to about 20, or about 4 to about 100. A PEG linker having n ranging from about 4 to about 100 may result in a spacer length of approximately 16 to 110 Å.

In certain embodiments, the polymer or oligomer may be water soluble, biocompatible and/or nonreactive. Biocompatability of the polymer or oligomer may, in at least certain embodiments, advantageously decrease the likelihood of interactions between the linking group and the enzyme, although it is not required. In various exemplary embodiments, the linking group comprises a PEG linker or a dextran. In yet further exemplary embodiments, the linking group comprises a PEG linker represented by Chemical Formula 4:

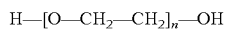

Chemical Formula 4

According to various exemplary embodiments, the at least one conjugative group chosen may lead to improved stability and/or resistance to enzymatic degradation, although it is not required.

In various exemplary embodiments, more than one conjugative group may optionally be chosen, where different conjugative groups have different properties. For example, multiple conjugative groups having different properties may be chosen for use in multiplexed assays. In certain embodiments using multiplexed arrays, different latent fluorophores may be connected to one or more types of supports by the same conjugative group.

Support

Supports useful according to various embodiments of the disclosure include, by way of non-limiting example, microspheres, microbeads, and beads, as well as any other support to which the compounds described herein can be attached. As used herein, the terms "microsphere," "microbead," and "bead," which may be used interchangeably herein to denote any particulate support, as well as variations thereof, mean a particle having a size ranging from about 0.1 µm to about 1000 µm.

It may be possible to increase the range of sensitivity in an assay by modifying properties of the support, and/or by choosing supports with a specific property or set of properties. For example, microspheres having larger or smaller diameters may be chosen, depending on the sensitivity desired. A high surface area of the support allows a large number of fluorophores to be attached thereto, which is thought to increase the operating range of the assay. As such, the number of latent fluorophores connected to the support, e.g. a microsphere, can be adjusted to achieve a desired operating range.

Further, supports having different functionalities, coatings, fluorescence excitation/emission characteristics, and/or scattering characteristics, may be chosen. One of skill in the art will be able to select a support having the appropriate properties, depending on, for example, the intended application and/or specific latent fluorophore comprising at least one enzyme-reactive quenching group and at least one conjugative group to be used.

In various exemplary embodiments, more than one support may be chosen, where different supports have different properties. For example, multiple supports having different properties may be chosen for use in multiplexed assays. In certain embodiments, different latent fluorophores may be connected to supports for use in multiplexed arrays.

By way of non-limiting example, more than one microbead having substantially the same properties constitutes a class or type of microbeads. Different classes or types of microbeads may be chosen where the microbeads have a variety of functionalities, fluorophores, and/or coatings. More than one class or type of microbeads measured simultaneously constitute a multiplexed array.

For example, SPHERO™ Blue Fluorescent Particle Kits (Spherotech, Lake Forest, Ill.) are available with carboxyl functionality for covalent attachment of ligands. These microbeads are produced with up to 10 different amounts of fluorescent dyes incorporated in them. Depending on the diameter of the beads, they are sold in kits of 7 to 10 individual classes of microbeads. The classes differ in fluorescence intensity in the PE-Cy5, allophycocyanin ("APC"), and APC-Cy7 channels with minimal fluorescence in the fluorescein isothiocyanate ("FITC") and R-phycoerythrin ("PE") channels, allowing identification of the beads' class. By using enzyme-reactive specific latent fluorophores which fluoresce in the FITC or PE channel (for example, rhodamine derivatives), the specific class of enzymatic activity can be identified by the fluorescence intensity of the bead in the PE-Cy5, APC, and APC-Cy7 channels.

As a further non-limiting example, microspheres having different fluorescence excitation/emission characteristics may be chosen. Examples include SPHERO™ Fluorescent Particles (Spherotech, Lake Forest, Ill.) and Fluorescent Microspheres (Bangs Laboratories, Fishers, Ind.).

A wide variety of fluorescent particles ranging in size, spectral characteristic of fluorescence, fluorescence lifetime, fluorescence intensity, and/or surface functional group are available. Classes of particles that differ in their spectral characteristic of fluorescence emission can be chosen to identify specific enzymatic activity, enzyme-reactive specific latent fluorophores which fluoresce in the FITC or PE channel that is associated with that class.

Depending on the application, the available excitation sources, and the emission filter(s) used, a variety of combinations can be selected. For example, available Internet tools such as the interactive spectrum viewer provided by BD Biosciences, Franklin Lakes, N.J., or the interactive spectrum viewer provided by Life Technologies Corporation, Carlsbad, Calif. can be used for dye selection. In at least certain embodiments, combinations may be chosen so that the emission characteristics (e.g., emission spectra) are sufficiently different so that a first emission spectrum (for example, from an enzyme-reactive latent fluorophore) does not significantly overlap with second and subsequent emission spectrum(a) (for example, fluorescent microspheres of type 1, type 2, and type 3).

By way of yet further non-limiting example, microspheres having different scattering characteristics may be chosen. In at least on exemplary embodiment, SPHERO™ Polystyrene Particles, Spherotech, Lake Forest, Ill., may be used in multiplex assays.

A wide variety of particle sizes with surface functional groups are available. For example, by linking a specific enzyme-reactive latent fluorophore (enzyme 1) to a bead of a specific size (microsphere type 1) and a second specific enzyme-reactive latent fluorophore (enzyme 2) to a bead of a different size (microsphere type 2), the specific enzyme activity (fluorescence from the latent fluorophore) can be associated with the scattering properties of the microsphere. The size of the beads may be selected so that there is a sufficient difference in the scattering properties of the various types of microspheres so that each can be uniquely identified.

In yet further exemplary embodiments, supports may be chosen that are coated. By way of example only, streptavidin-coated microspheres may be used in various embodiments of the disclosure. In yet further, non-limiting exemplary embodiments, other binding proteins, or either component of any conjugative linking pair, may be coated on the support.

Magnetic Support

In at least certain exemplary embodiments according to the disclosure, magnetic microspheres, microbeads, and beads may be chosen as the support for the latent fluorophore. As used here, the terms "magnetic microsphere," "magnetic microbead," and "magnetic bead," which may be used interchangeably, as well as variations thereof, mean a particle exhibiting magnetism. For the manipulation of beads, paramagnetism or superparamagnetism in the presence of an externally applied magnetic field is often used. Paramagnetic materials exhibit a positive change in magnetic moment in the presence of an externally applied magnetic field. Superparamagnetic materials exhibit high levels of paramagnetism. The high levels of paramagnetism exhibited in superparamagnetic materials are due to microscale or nanoscale ordering of spin orientations, which may be lacking in other paramagnetic materials. In certain exemplary embodiments, the support comprises a superparamagnetic material.

Sizes of commercially available magnetic beads typically range from about 0.1 µm to about 120 µm. They often contain a paramagnetic material, for example iron oxide, resulting in the beads' paramagnetic properties, and a biocompatible shell that can be functionalized. The paramagnetic material may constitute the core of the particle or may be a shell-like coating on a core, for example made of polystyrene. However, it should be noted that magnetic supports useful according to the disclosure are not required to have any particular size, functionality, and the like, such as found in commercially available products.

Because of their embedded paramagnetic materials, such beads can be manipulated by an external magnetic field that induces a non-negligible magnetic field in the bead. In particular, the beads can be moved through a solution, collected, dispersed, mixed and extracted in a controlled manner by means of an applied external magnetic field. Paramagnetic beads have the advantage of a magnetic field that vanishes once the external field vanishes, so that the beads do not influence each other in undesirable ways, for example cluster together. Methods for controlled sample preparation involving such magnetic beads are known in the art.

Additionally, fluorophores can be embedded in the bead for detection or identification (for example UMC3F COMPEL™ Magnetic COOH modified, fluorescent particles from Bangs Laboratories Inc.). Connecting a fluorophore to a magnetic microsphere may allow concentration of the fluorescence signal after performing an enzymatic reaction in a larger volume. The technique can allow the enzyme assay to be performed in complex solutions, for example whole blood. It also enables efficient rinsing of interfering compounds, components, and the like, prior to detecting the fluorescence signal. In addition, fluorophores connected to magnetic microspheres can, in at least certain exemplary embodiments, enable automated sample preparation and analysis.

Methods of Preparing Latent Fluorophores Linked to a Support

Any known method for preparing latent fluorophores comprising at least one enzyme-reactive group and at least one conjugative group may be used. It is well within the skill of those in the art to design appropriate chemical reactions in order to prepare a latent fluorophore having at least one enzyme-reactive group and at least one conjugative group.

An exemplary and non-limiting method of synthesizing a latent fluorophore represented by Chemical Formula 1, which method is presented solely for purposes of illustrating one optional embodiment, is shown in Reaction Scheme 1.

Reaction Scheme 1

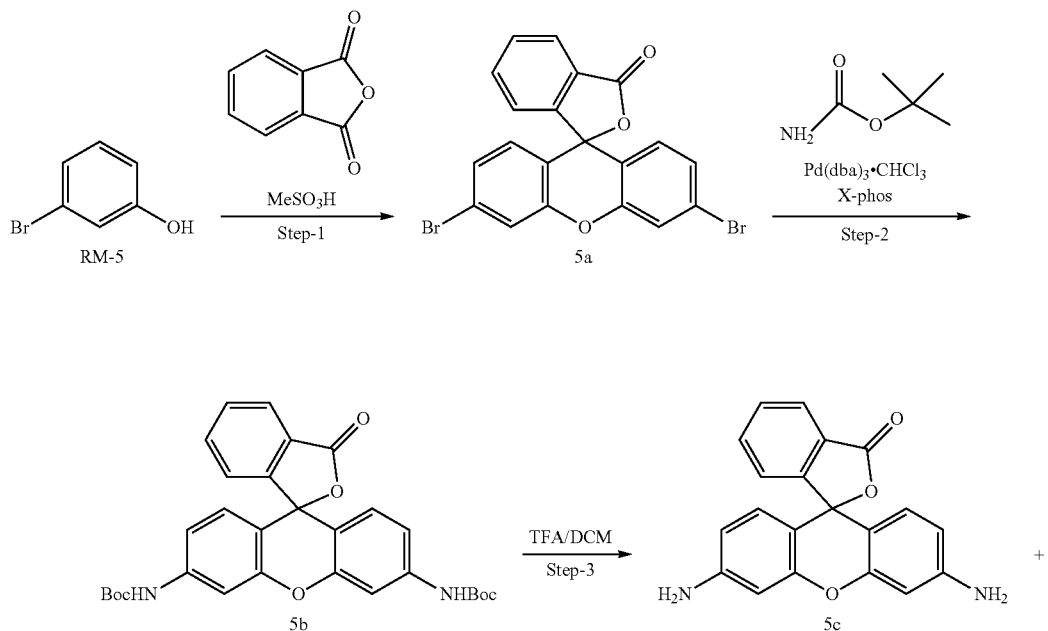

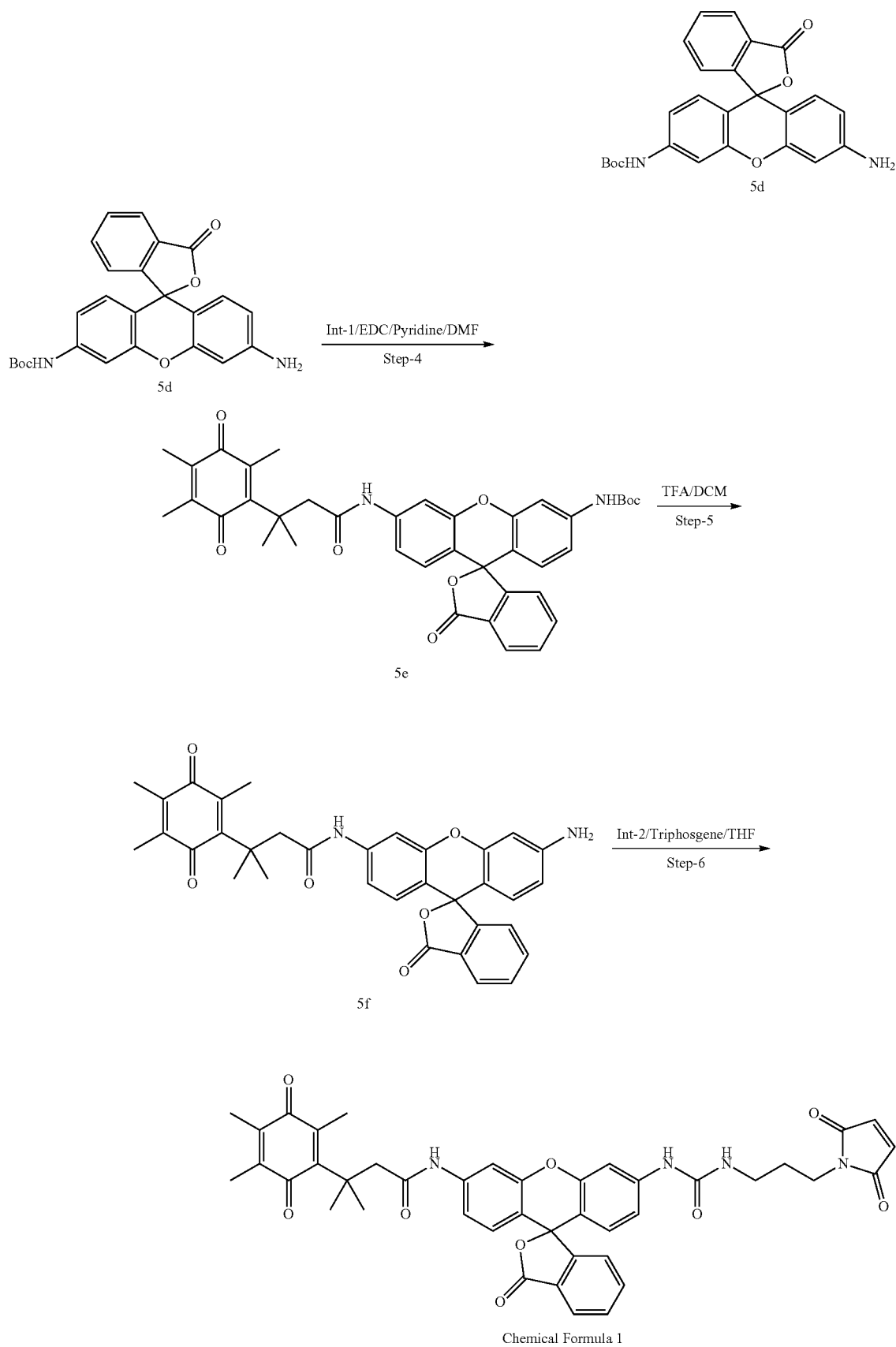

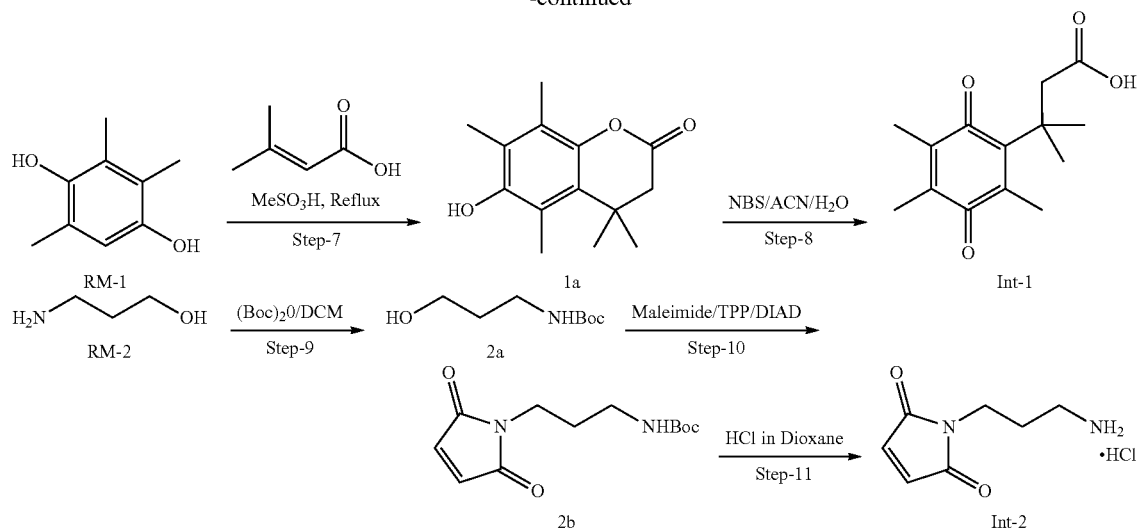

Any known connection between a support and latent fluorophores comprising at least one enzyme-reactive group and at least one conjugative group is also contemplated to be within the scope of the disclosure. By way of non-limiting example only, a latent fluorophore such as that of Chemical Formula 1 prepared according to Reaction Scheme 1 may be linked to the microsphere with a PEG linker. For example, a heterobifunctional PEG may be chosen, such as thiol-PEG-Amine (e.g. HS-PEG-NH$_2$; Creative PEGworks, Winston Salem, N.C.). The thiol group reacts with the maleimide group on Chemical Formula 1, the amine group is reacted with a microsphere containing a carboxylic acid functionality (for example, Dynabeads® M-270 Carboxylic Acid (magnetic, nonfluorescent) or FluoSpheres® Carboxylate-Modified Microspheres (fluorescent, nonmagnetic), both Life Technologies Corporation, Carlsbad, Calif.; Polybead® Carboxylate Microspheres (nonfluorescent, nonmagnetic) or Fluoresbrite® BB Carboxylate Microspheres (fluorescent, nonmagnetic); both Polysciences, Inc., Warrington, Pa.)) following activation with 1-ethyl-3-(3-dimethylaminopropyl) carbodiimide hydrochloride (EDC) to yield the desired latent fluorophore linked to a microsphere. Optionally, the amine group at the end of the PEG linker on the latent fluorophore can be linked to a Tosylactivated microsphere (for example, Dynabeads® M-280 Tosylactivated; Life Technologies Corporation, Carlsbad, Calif.).

In yet a further non-limiting exemplary embodiment where the latent fluorophore is chosen from those of Chemical Formula 2, thiol-PEG-acid may be chosen (e.g. HS-PEG-COOH; Creative PEGworks, Winston Salem, N.C.) to link to the support. The thiol group is reacted with the maleimide group on Chemical Formula 2, the carboxylic acid group is reacted with 1-Ethyl-3-[3-dimethylaminopropyl]carbodiimide hydrochloride (EDC) and crosslinked to a microsphere containing a carboxylic acid functionality (for example, Dynabeads® M-270 Carboxylic Acid; Life Technologies Corporation, Carlsbad, Calif., or Polybead® Carboxylate Microspheres; Polysciences, Inc., Warrington, Pa.).

In yet a further exemplary embodiment for preparing latent fluorophores and linking to a support, the latent fluorophores comprising at least one enzyme-reactive group and at least one conjugative group may be synthesized with a biotin group as at least one conjugative group. The latent fluorophore-biotin compound may then be reacted with streptavidin-coated microspheres, to yield a latent fluorophore linked to a microsphere.

Further, any known method of linking latent fluorophores comprising at least one enzyme-reactive group and at least one conjugative group to a support is also contemplated to be within the scope of the disclosure. In certain exemplary embodiments, the latent fluorophores may spontaneously connect to the support when both are placed in solution. In further exemplary embodiments, the solution may be stirred, heated, and/or cooled to facilitate the linkage between the fluorophore and the support. In yet further exemplary embodiments, additives, for example surfactants, promoting agents, enzymes and the like, may be added to the solution to facilitate the linkage between the fluorophore and the support.

Methods of Using Latent Fluorophores Linked to a Support

As used herein, the term "measuring enzyme activity" and variations thereof refers to a measure of the quantity of active enzyme, and/or of the quantity of analyte acted upon by the enzyme. As used herein, the terms "an enzyme reacting with the analyte," "an enzyme acting upon the analyte," and variations thereof mean a chemical reaction catalyzed by an enzyme, wherein an analyte is chemically altered. In certain embodiments, the chemical reaction may be a dehydrogenation reaction.

The fluorophore compositions described according to various embodiments of the disclosure may be useful in enzyme assays. For example, the fluorophore compositions may be useful for methods of measuring activities of enzymes. In various embodiments, the fluorescence signal of the unlocked fluorophore may be proportional to the enzyme activity to be measured due to the quenching group being altered and/or released by the enzyme in question, and/or by a downstream enzyme in a series of enzyme reactions, or enzyme cascade, including the enzyme in question. In certain embodiments, the enzyme activities of two or more enzymes may be compared.

Further, the fluorophore compositions may be useful for detecting and/or measuring the concentration of analytes in a sample, for example when the enzyme activity of a known concentration of enzyme in the presence of an unknown amount of analyte is compared with the enzyme activity of a known concentration of enzyme in the presence of a known amount of analyte.

As used herein, a sample may be any substance, in particular a sample of liquid substance, and in at least certain embodiments, may be a sample of bodily fluids such as urine, saliva, or blood. The samples used according to various methods described herein may be obtained or collected by any technique known. A "test" sample and a "reference" sample may, in at least certain embodiments, be two samples from the same source, e.g. two samples of blood taken from one blood collection, where the test sample and reference sample may be treated with the compositions described herein in different manners.

Methods of Measuring the Activities of Enzymes

Enzymatic activity dependent on the presence of a particular substrate is known to be correlatable with the concentration of that substrate. Compositions prepared according to various embodiments of the disclosure may permit detection of such enzymatic activity via enzymatic assay. Exemplary enzyme assays useful according to various embodiments include, but are not limited to, enzyme cascade assays, coupled assays and direct assays.

As used herein, the terms "contact," "contacting," and variations thereof mean bringing components into close enough proximity to allow for a chemical or enzymatic reaction to occur between or among the components. The contacting may be between or among any combination of components in any manner. In various non-limiting exemplary embodiments, the contacting between a sample and a fluorophore is performed by including or mixing a fluorophore in a liquid sample. In certain embodiments, the liquid sample may be stirred, sonicated, heated and/or cooled, and/or additives may be added to the liquid sample to facilitate the contacting between the sample and the fluorophore.

As used herein, the terms "compare," "comparing," and variations thereof mean determining the relative quantitative and/or qualitative fluorescence signals of two or more samples, by any method, and including either human or machine/computer determination. The fluorescence signals of the samples may be compared by any known methods. In one non-limiting exemplary embodiment, the fluorescence signals of two samples may be compared by subtracting the quantitative signal of one sample from the quantitative signal of the other sample.

Methods for measuring the activity and/or presence of an enzyme in a test sample including an analyte include one or more steps chosen from:
 a. preparing a fluorophore composition comprising:
  i. at least one enzyme-reactive latent fluorophore comprising at least one enzyme-reactive quenching group and at least one conjugative group, and
  ii. a support connectable to the latent fluorophore by at least one conjugative group;
 b. providing a test sample to be analyzed and a reference sample to be analyzed, wherein the reference sample contains a known quantity of the analyte;
 c. contacting the test sample with the latent fluorophore composition, at least one first unquenching enzyme capable of releasing the enzyme-reactive quenching group from the latent fluorophore, and at least one second enzyme capable of reacting with the analyte;
 d. contacting the reference sample with the latent fluorophore composition and the at least one first unquenching enzyme;
 e. measuring the fluorescence signal of the test sample and the fluorescence signal of the reference sample; and
 f. comparing the fluorescence signal of the test sample with the fluorescence signal of the reference sample.

In various embodiments of the method of measuring the activity of an enzyme, the first unquenching enzyme that unlocks the latent fluorophore added to the test sample may be the same as or different from the second enzyme capable of reacting with the analyte. When the first unquenching enzyme is the same as the second enzyme, this may be referred to as a direct assay. When the first unquenching enzyme is different from the second enzyme, this may be referred to as an enzyme cascade or coupled assay, and in various embodiments the first enzyme may be considered downstream of the second enzyme because the first enzyme uses a by-product of the reaction between the second enzyme and the analyte in order to unquench the quenching group.

By way of non-limiting example, in one embodiment the first unquenching enzyme that unlocks the latent fluorophore added to the test sample is the same as the first unquenching enzyme added to the reference sample. When the same enzyme is added to both samples, the resulting difference in fluorescence may be attributed to the activity of the enzyme on the analyte, when the only difference between the test sample and the reference sample is the quantity of analyte. In certain exemplary embodiments, the reference sample is free or substantially free of the analyte. In contrast, in a non-limiting embodiment where the test sample includes a different unquenching enzyme than the unquenching enzyme in the reference sample, a difference in fluorescence signal between the two samples may be at least partially attributable to the difference in unquenching activity and/or rate between different unquenching enzymes.

Methods for measuring activities of two or more enzymes in a sample, for example in a multiplex assay, include one or more steps chosen from:
 a. providing a first fluorophore composition comprising:
  i. at least one first enzyme-reactive latent fluorophore comprising at least one first enzyme-reactive quenching group and at least one conjugative group, and
  ii. at least one support connectable to the at least one first latent fluorophore by at least one conjugative group;
 b. providing a second fluorophore composition comprising:
  i. at least one second enzyme-reactive latent fluorophore comprising at least one second enzyme-reactive quenching group and at least one conjugative group, wherein the at least one second enzyme-reactive latent fluorophore is different from said first enzyme-reactive latent fluorophore in said first fluorophore composition, and
  ii. at least one support connectable to the at least one first latent fluorophore by at least one conjugative group;
 c. providing a test sample to be analyzed and a reference sample to be analyzed;
 d. contacting the test sample with the first and second latent fluorophore compositions, at least one first unquenching enzyme capable of releasing the enzyme-reactive quenching group from the first latent fluorophore, and at least one second unquenching enzyme capable of releasing the enzyme-reactive quenching group from the second latent fluorophore;
 e. contacting the reference sample with the first and second latent fluorophore compositions;
 f. measuring the fluorescence signals of the test sample and the fluorescence signals of the reference sample; and
 g. comparing the fluorescence signals of the test sample with the fluorescence signals of the reference sample.

In various embodiments of the method of the multiplex assay above, the first unquenching enzyme that unlocks the latent fluorophore added to the test sample may be the same as or different from the first enzyme added to the reference sample. When the first unquenching enzyme is the same as the first enzyme, this may be referred to as a multiplex direct assay. When the first unquenching enzyme is different from the first enzyme, this may be referred to as a first enzyme cascade, at in various embodiments the first unquenching enzyme may be considered downstream of the first enzyme because the first unquenching enzyme uses a by-product of the reaction between the first enzyme and the analyte in order to unquench the first quenching group. An enzyme cascade including two enzymes, one that reacts with the analyte and the other that unquenches the latent fluorophore, may be referred to as a coupled assay.

By way of example, in one non-limiting embodiment, the first quenching group is different from the second quenching group. For a multiplex direct assay, wherein the analyte-active enzyme is the same as the unquenching enzyme, the first and second quenching groups are unlocked by different unquenching enzymes; otherwise the difference in fluorescence signal could not be correlated with the activity of a particular enzyme on a particular analyte. For a multiplex enzyme cascade assay, wherein an enzyme having activity in the presence of an analyte is part of an enzyme cascade that includes a downstream unquenching enzyme, the first and second quenching groups are unlocked by different unquenching enzymes; otherwise the difference in fluorescence signal could not be correlated with the activity of a particular enzyme cascade on a particular analyte.

In various embodiments, the first fluorophore has a first emission spectrum that may be the same as or different from a second emission spectrum of the second fluorophore. When the first and second emission spectra have at least one different property, for example peak emission wavelength, peak absorption wavelength, and/or fluorescence lifetime, the first and second fluorescence signals from the first and second fluorophores, respectively, may be distinguished.

Alternatively, when the first and second emission spectra are the same, the first fluorophore may be distinguished from the second fluorophore by employing other techniques. In various embodiments, one such technique includes physically separating the first fluorophore from the second fluorophore, for example by linking at least one of the fluorophores to a support and physically separating the support, for example by spatial concentration using an external magnetic, electric or acoustic field, or filtering; and/or linking the first fluorophore to a first support and the second fluorophore to the second support, and subsequently distinguishing the first support and the second support. In certain embodiments, the first support and the second support may be distinguished by the differential fluorescence of the first and second supports, and/or by differential scattering by first and second supports having different sizes.

In certain embodiments of the multiplex assay method above, the conjugative group linking the first fluorophore to the support may be the same as or different from the conjugative group linking the second fluorophore to the support. By way of non-limiting example, in one embodiment the conjugative group may be different in order to selectively link one of the fluorophores with a support, while the other fluorophore is linked to a different support or left freely suspended in the test or reference sample. In other non-limiting exemplary embodiments, the conjugative group is the same for both the first and second fluorophores, for example when the fluorophores are linked to the same or different support temporally and/or spatially independently of one another, when the fluorophores are linked to the same support, and/or when the fluorophores have sufficiently distinct fluorescence signals that separation of the fluorophores during the fluorescence measurement is not necessary.

In various embodiments of the multiplex assay method above, the first fluorophore and the second fluorophore may be linked to the same support, the same type of support, a different support, or a different type of support.

By way of example, a coupled assay may include at least one first enzyme that generates a first reaction product from a first enzymatic reaction on a first substrate, and at least one second enzyme that uses the first reaction product generated from the first enzymatic reaction to produce a fluorescence signal by reacting with and releasing the enzyme-reactive quenching group on the latent fluorophore. In certain embodiments, the fluorescence signal may be approximately proportional to the concentration of the first substrate.

According to various exemplary and non-limiting embodiments of the disclosure, the at least one first enzyme may be chosen from protease, phosphatase, and dehydrogenase. In at least one exemplary embodiment, the first enzyme is a dehydrogenase, and the first enzymatic reaction is a dehydrogenation reaction. In certain embodiments, the first substrate is phenylalanine, the first enzyme is phenylalanine dehydrogenase, and the first reaction products are NADH (or NADPH)+phenylpyruvate+$NH_3$+$H^+$. The first substrate, first enzyme, and first reaction products for other exemplary embodiments are shown in Table 1 below.

TABLE 1

| First Substrate | First Enzyme | First Reaction Product |
|---|---|---|
| Cholesterol | Cholesterol dehydrogenase | NADH + cholest-4-en-3-one + $H^+$ |
| Lactate | Lactate dehydrogenase | NADH + pyruvate + $H^+$ |
| Leucine | Leucine dehydrogenase | NADH + 4-methyl-2-oxopentanoate + $NH_3$ + $H^+$ |
| D-glucose | Glucose dehydrogenase | NADH + D-glucono-1,5-lactone + $H^+$ |
| Ethanol | Alcohol dehydrogenase | NADH + acetaldehyde |

Other non-limiting examples of enzymes contemplated according to various embodiments of the disclosure may use modification of an enzyme-reactive group to achieve specificity for the enzyme of interest, for example alkaline phosphatase using a rhodamine fluorophore (Levine, M. N. et al, Analytical Biochemistry 418 (2011), 247-252); esterase (Levine, M. N. et al, Molecules (2008), 13, 204-211); and serine protease using a bis(N-benzyloxycarbonyl-L-argininamido)Rhodamine substrate (Leytus, S. P. et al, Biochem. J (1983), 209, 299-307).

According to various exemplary embodiments, the at least one second enzyme may be a diaphorase. As used here, the term "diaphorase" is intended to encompass several different enzyme classes, some of which have different substrate specificities for NADH or NADPH. By way of example only, the diaphorase may be chosen from the enzyme classes EC 1.8.1.4—dihydrolipoyl dehydrogenase, EC 1.6.5.2—NAD(P)H dehydrogenase (quinone or DT-diaphorase), EC 1.6.99.1—NADPH dehydrogenase, EC 1.6.99.3—NADH dehydrogenase, and mixtures thereof, all of which may catalyze oxidation/reduction reactions. In at least one exemplary embodiment, the diaphorase may be chosen from dihydrolipoyl dehydrogenase and NAD(P)H dehydrogenase.

As shown in FIG. 1, an exemplary coupled assay for measuring the amount of an analyte in a sample may include a dehydrogenase and a diaphorase. In this exemplary embodiment, the dehydrogenase reacts with the analyte in the sample to produce an oxidized analyte and NADH in a dehydrogenase reaction. The diaphorase uses the NADH created by the dehydrogenase reaction to react with and release the enzyme-reactive quenching group from the latent fluorophore, thus revealing a fluorescent compound.

In various embodiments, the concentrations of dehydrogenase and diaphorase may be adjusted such that the oxidation of the analyte is the rate-limiting reaction.

Figure 2:
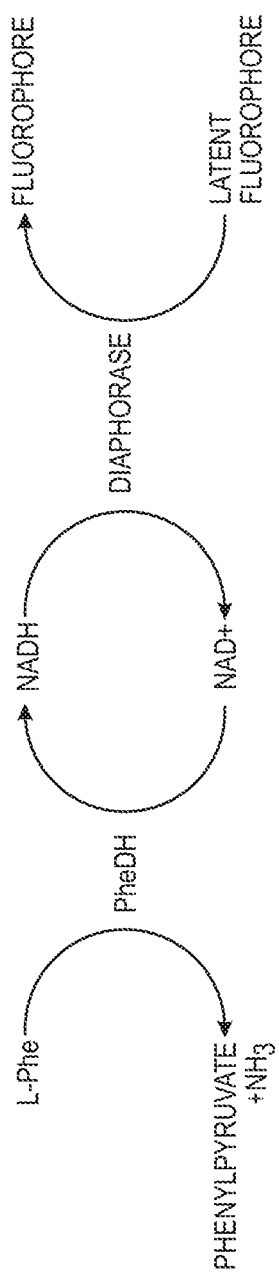
FIG. 2 is an exemplary schematic of a coupled assay for detecting phenylalanine according to an embodiment of the disclosure.

As shown in FIG. 2, an exemplary coupled assay for measuring the amount of phenylalanine in a sample may include a phenylalanine dehydrogenase (PheDH) and a diaphorase. In this embodiment, the PheDH reacts with phenylalanine in the sample to produce phenylpyruvate, NH$_3$ and NADH in a dehydrogenase reaction. The diaphorase uses the NADH created by the dehydrogenase reaction to react with and release the enzyme-reactive quenching group from the latent fluorophore, thus revealing a fluorescent compound.

In various embodiments, the concentrations of PheDH and diaphorase may be adjusted such that the oxidative deamination of phenylalanine is the rate-limiting reaction.

In various exemplary embodiments, a direct assay may include at least one enzyme that acts upon a substrate to produce a fluorescence signal by reacting with and releasing the enzyme-reactive quenching group on the latent fluorophore. In at least one exemplary embodiment, the enzyme may be pyruvate oxidase and the substrate may be pyruvate.

Figure 3:
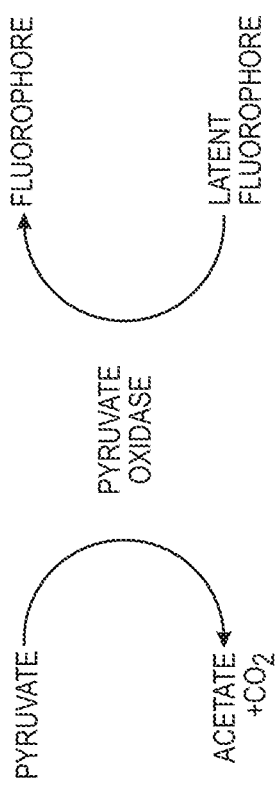
FIG. 3 is an exemplary schematic of a direct assay for detecting an analyte.

As shown in FIG. 3, an exemplary direct assay for measuring the amount of pyruvate in a sample includes a pyruvate oxidase. In this exemplary embodiment, the pyruvate oxidase reacts with the pyruvate in the sample to produce acetate and CO$_2$, and also reacts with and releases a quinone enzyme-reactive quenching group from the latent fluorophore, thus revealing a fluorescent compound.

Methods of Detecting and Measuring Analytes in a Sample

Enzyme-reactive latent fluorophores linked to microspheres prepared according to various embodiments described herein may, in exemplary embodiments, be used to detect the presence and/or concentration of certain analytes in a sample. The analyte may, for example, be detected by utilizing a direct or coupled assay.

Exemplary methods for detecting and measuring an analyte in a sample include one or more steps chosen from:
a. preparing a fluorophore composition comprising:
  i. at least one enzyme-reactive latent fluorophore comprising at least one enzyme-reactive quenching group and at least one conjugative group, and
  ii. a support connectable to the latent fluorophore by at least one conjugative group;
b. providing a test sample to be analyzed and a reference sample to be analyzed;
c. contacting the test sample with the latent fluorophore composition, at least one first unquenching enzyme capable of releasing the enzyme-reactive quenching group from the latent fluorophore, and at least one second enzyme capable of reacting with the analyte;
d. contacting the reference sample with the latent fluorophore composition and the at least one first unquenching enzyme;
e. measuring the fluorescence signal of the test sample and the fluorescence signal of the reference sample; and
f. comparing the fluorescence signal of the test sample with the fluorescence signal of the reference sample.

In various embodiments of the method of measuring the activity of an enzyme above, the first unquenching enzyme that unlocks the latent fluorophore added to the test sample is the same as or different from the second enzyme capable of reacting with the analyte. When the first unquenching enzyme is the same as the second enzyme, this may be referred to as a direct assay. When the first unquenching enzyme is different from the second enzyme, this may be referred to as an enzyme cascade or coupled assay, wherein the first enzyme is considered downstream of the second enzyme because the first enzyme requires a by-product of the reaction between the second enzyme and the analyte in order to unquench the quenching group.

By way of non-limiting example, an assay, e.g. a coupled assay, may be used to measure the presence and/or concentration of phenylalanine in whole blood. In at least certain exemplary embodiments, an assay, e.g. a coupled assay, can be used to measure the presence and/or concentration of any analyte in any solution, e.g. those that have a specific dehydrogenase that generates NADH or NADPH in a solution, for example whole blood. In various embodiments, the assay can be used to measure the presence and/or concentration of a metabolite, for example a human metabolite or an animal metabolite, in a bodily fluid, for example blood, urine, saliva, bile, spinal fluid, gastric juices, mucus, tears, amniotic fluid, semen, sweat, lymph fluids, and the like.

Figure 4A:
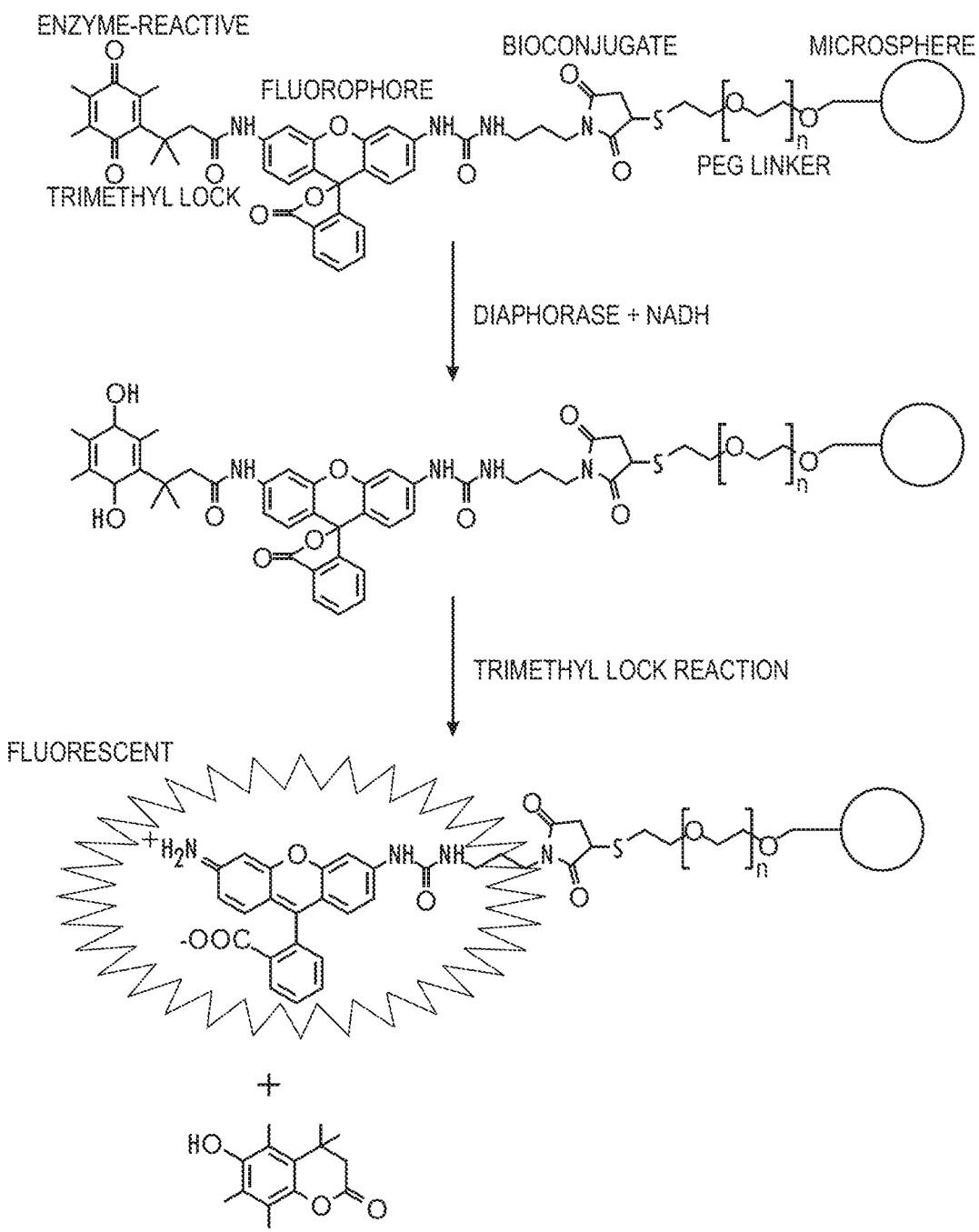
FIG. 4A is an exemplary reaction schematic showing a latent fluorescent compound revealed by a trimethyl lock reaction according to an embodiment of the disclosure.

FIG. 4A is an exemplary reaction schematic showing a latent fluorescent compound revealed by a trimethyl lock reaction. In this exemplary embodiment, the latent fluorophore having an enzyme-reactive quenching group is connected to a microsphere with a linking group including a pyrrole-2,5-dione bioconjugate and a PEG linker. In the presence of a suitable enzyme, for example diaphorase, and any cofactors, for example NADH, the enzyme-reactive quenching group is released from the latent fluorophore via a trimethyl lock reaction. The fluorophore connected to the microsphere is now fluorescent.

Figure 4B:
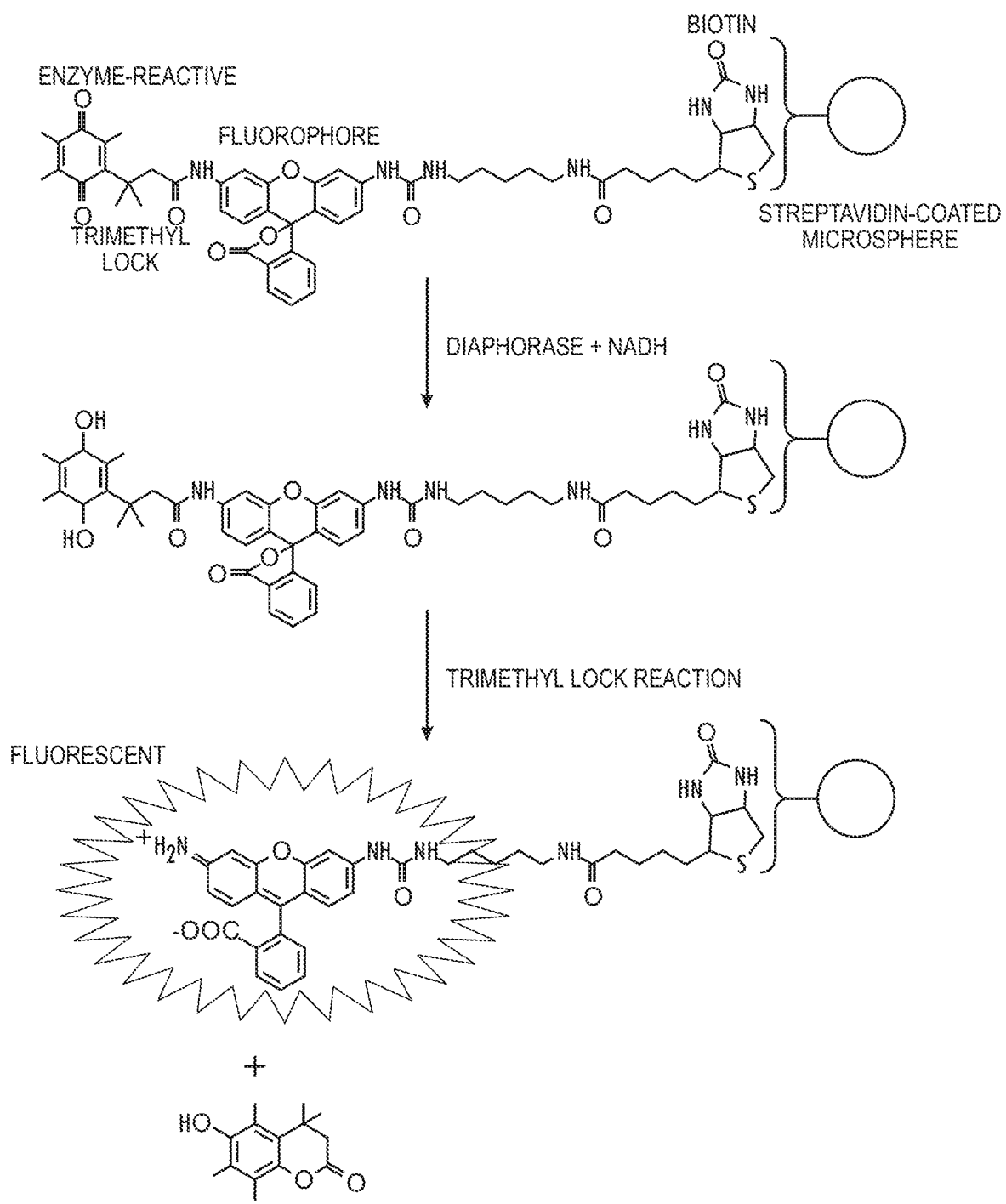
FIG. 4B is an exemplary reaction schematic showing a latent fluorescent compound revealed by a trimethyl lock reaction and connected to a microsphere with a biotin-streptavidin linkage according to an embodiment of the disclosure.

FIG. 4B is an exemplary reaction schematic showing a latent fluorescent compound revealed by a trimethyl lock reaction and connected to a microsphere with a biotin-streptavidin linkage. In this exemplary embodiment, the latent fluorophore having an enzyme-reactive quenching group and a biotin group is connected to a microsphere coated with streptavidin. In the presence of a suitable enzyme, for example diaphorase, and any cofactors, for example NADH, the enzyme-reactive quenching group is released from the latent fluorophore via a trimethyl lock reaction. The fluorophore connected to the microsphere is now fluorescent.

Figure 5:
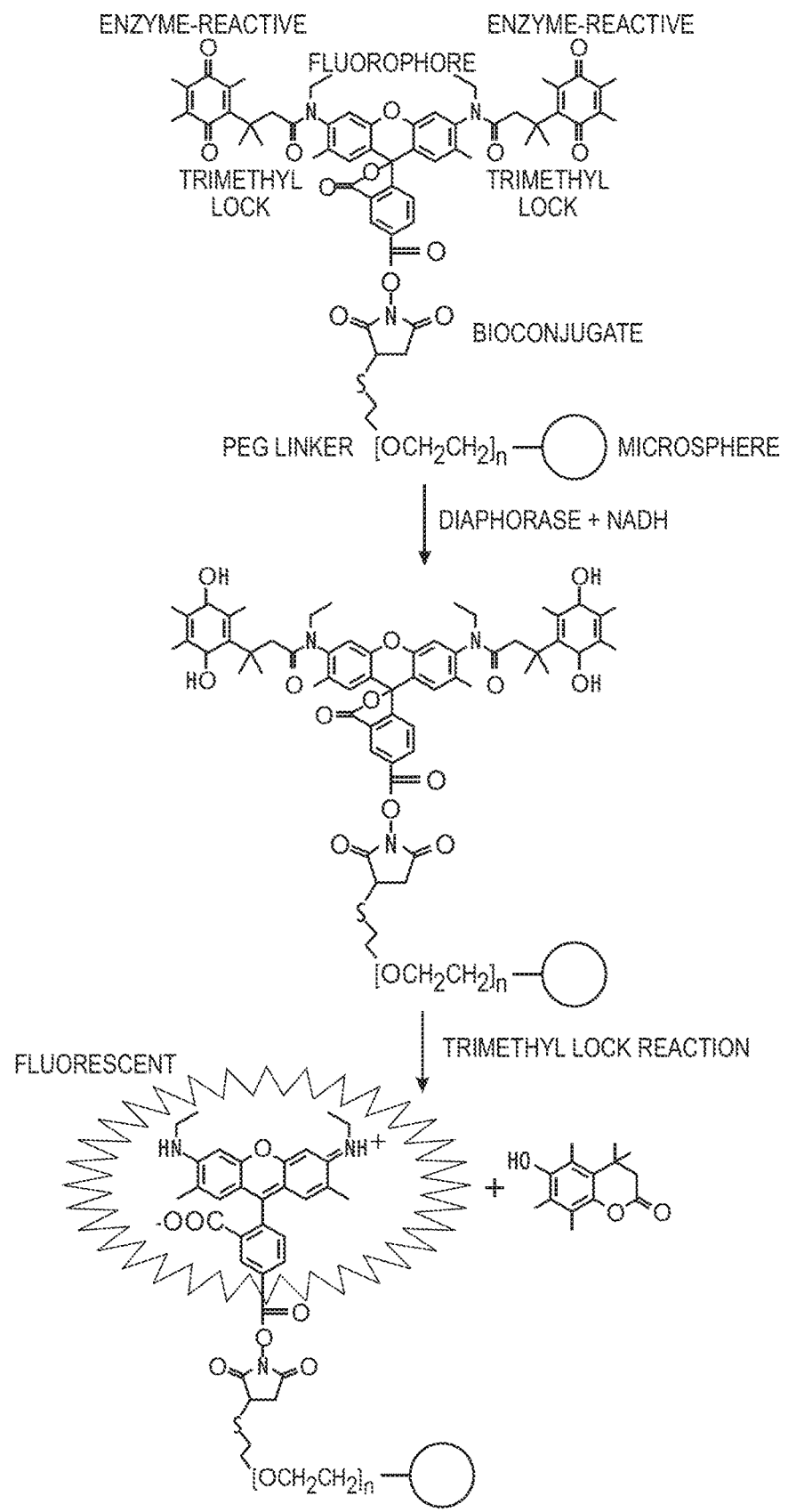
FIG. 5 is an exemplary reaction schematic showing a latent fluorescent compound revealed by a double trimethyl lock reaction according to an embodiment of the disclosure.

FIG. 5 is an exemplary reaction schematic showing a latent fluorescent compound revealed by a double trimethyl lock reaction. In this exemplary embodiment, the latent fluorophore has two enzyme-reactive quenching groups, and is connected to a microsphere with a linking group including a pyrrole-2,5-dione bioconjugate and a PEG linker. In the presence of an enzyme, for example diaphorase, and any necessary cofactor, for example NADH, the enzyme releases one or both of the enzyme-reactive groups. In certain embodiments, having two enzyme-reactive groups can help increase or maximize the difference in fluorescence intensity upon reaction with the enzyme.

In various embodiments, the microspheres may be used to isolate the fluorophores from the sample solution prior to the fluorescence measurement. In at least one embodiment, fluorophores connected to magnetic microspheres may be collected using a magnet, and the other reactants, compounds, and materials in the sample may be washed away. In certain embodiments, the isolated magnetic microspheres may be suspended in a suitable buffer, for example phosphate-buffered saline. The fluorescence of the fluorophores linked to the magnetic microspheres can then be then measured.

The fluorescence of the active fluorophore may be measured by any known process, including but not limited to bulk fluorescence, flow cytometry, or spatially modulated fluorescence detection technology.

In certain exemplary and non-limiting embodiments according to the disclosure, the fluorescence signal may be measured using bulk fluorescence measurements. In certain embodiments, fluorescence in the sample may be induced by directing light of an appropriate wavelength region into the sample that contains the fluorophores. Fluorescent light of longer wavelengths than the excitation light may be collected and detected from the same sample region. To block out unwanted excitation light from the detection path, the optical axis of excitation and detection path may be arranged perpendicularly or in opposing direction (so called epi-detection). Additionally, excitation and background light can be separated and filtered with wavelength selective (dichroic) mirrors and filters, for example bandpass filters.

In yet further exemplary embodiments, the fluorescence signal may be measured using flow cytometry, the principles of which are well known, and thus one of skill in the art would be able to determine the appropriate procedures and/or parameters for use according to various embodiments of the disclosure.

In flow cytometry, the same measurement principles as in bulk fluorescence detection are applied. However, rather than measuring bulk fluorescence, the fluorescence intensity of particles is detected in a flow cytometer. The excitation and detection region of a flow cytometer are placed in the path of particles that are transported through a fluidic system. The excitation/detection region covers usually the lateral width of the flow channel and expands some tens of micrometers along the flow direction. Typical particle sizes detected in a flow cytometer generally range from 100s nm to 10 s of µm. The size of the excitation/detection region is limited in flow direction to ensure that ideally only a single particle is present in this region at any given time. Commonly, flow cytometers can excite and detect in several wavelength regions, including scattered light at the excitation wavelength. The subsequent (fluorescence) intensity measurement of hundreds, thousands or even ten thousands of particles contains the statistical information of the basic population.

In flow cytometry it is common practice to measure particle sizes by forward scattering signals. This measurement requires a precise alignment of the excitation laser and the detector by a light block. This block prevents laser light from entering the detector when no particle is present. A particle with a refractive index ("RI") different from the suspension solution may scatter light within the excitation spot of the laser. This scattered light is detected by the scatter detector, because it passes by the sides of the light block. The intensity of the scattered light depends on a variety of particle properties, including RI, size, and scatter center distribution. In a forward scattering direction, the amount of scattered light is usually a measure of particle size, as the RI of bioparticles does not differ from bioparticle type to bioparticle type enough to provide relevant bioparticle information while size (shape, orientation) dominates the scatter properties of the particle.

In yet further exemplary embodiments, the fluorescence signal may be measured using spatially modulated fluorescence detection technology, which uses fluorescence detection comparable to a flow cytometer. However, the spatial modulation technique uses a large excitation/detection area (ca. 0.1×1 mm) to increase the total flux of fluorescence light that originates from a particle. This configuration generates a time-dependent signal as a continuously fluorescing particle traverses a predefined pattern for optical transmission. Correlating the detected signal with the known pattern achieves high discrimination of the particle signal from background noise and simplifies optical system alignment. At the same time, multiple particles that simultaneously occur in the detection region can be differentiated computationally by the correlation of the signal sequences and the known transmission mask pattern.

Figure 6:
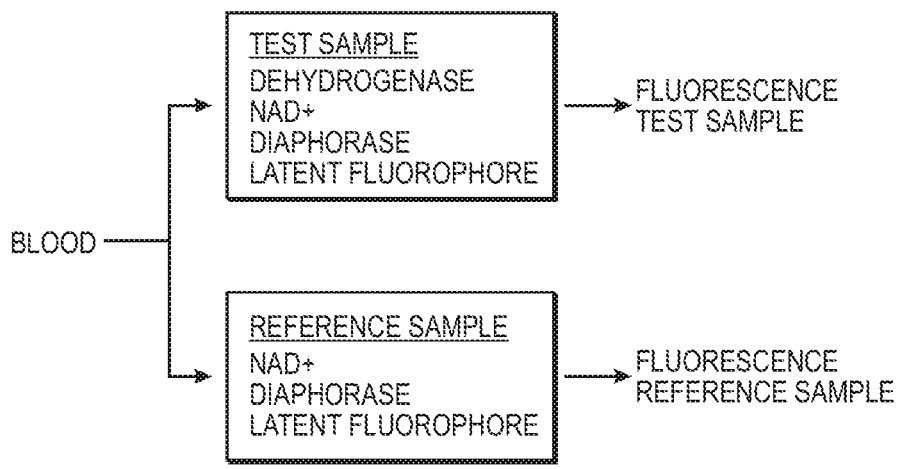
FIG. 6 is a flowchart showing the steps for a general dehydrogenase differential assay according to an exemplary embodiment of the disclosure.

FIG. 6 is a flowchart showing the steps for an exemplary dehydrogenase differential assay of a sample, for example blood. The sample is divided between a test sample and a reference sample. The test sample contains the analyte-specific enzyme, for example dehydrogenase, the diaphorase, the latent fluorophore, plus any necessary cofactors, for example NAD+. The reference sample contains all of the components in the test sample except for the analyte-specific enzyme. The fluorescence signals from the test sample and the reference sample are measured, and the fluorescence signal of the reference sample is subtracted from that of the test sample to yield a differential measurement.

In certain embodiments, differential measurements may be desired, e.g. to increase the reliability of the assay. For example, some individuals may have varying levels of other analytes in their blood, which can result in different background signals that are independent of enzymatic action on the desired analyte.

Figure 7:
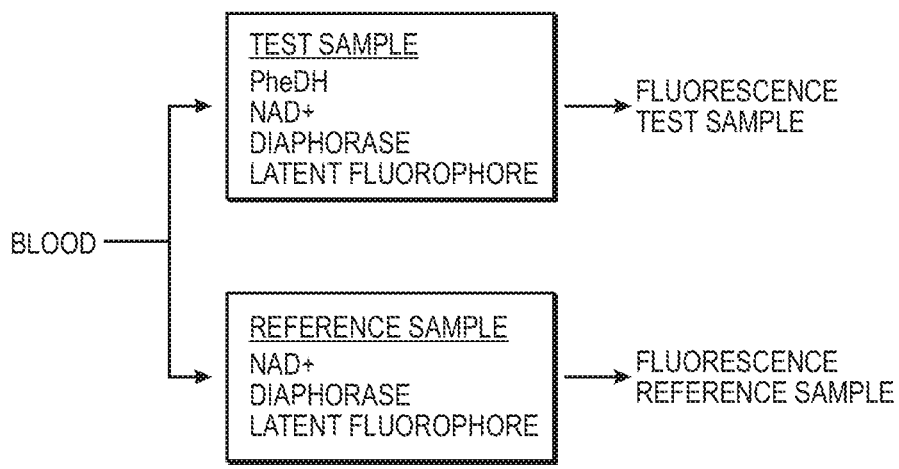
FIG. 7 is a flowchart showing the steps for a phenylalanine dehydrogenase differential assay according to an exemplary embodiment of the disclosure.

FIG. 7 is a flowchart showing the steps for an exemplary phenylalanine dehydrogenase differential assay of blood. The sample is divided between a test sample and a reference sample. The test sample contains phenylalanine dehydrogenase (PheDH), the diaphorase, the latent fluorophore, plus any necessary cofactors, for example NAD+. The reference sample contains all of the components in the test sample except for the PheDH. The fluorescence signals from the test sample and the reference sample are measured, and the fluorescence signal of the reference sample is subtracted from that of the test sample to yield a differential measurement.

Figure 8:
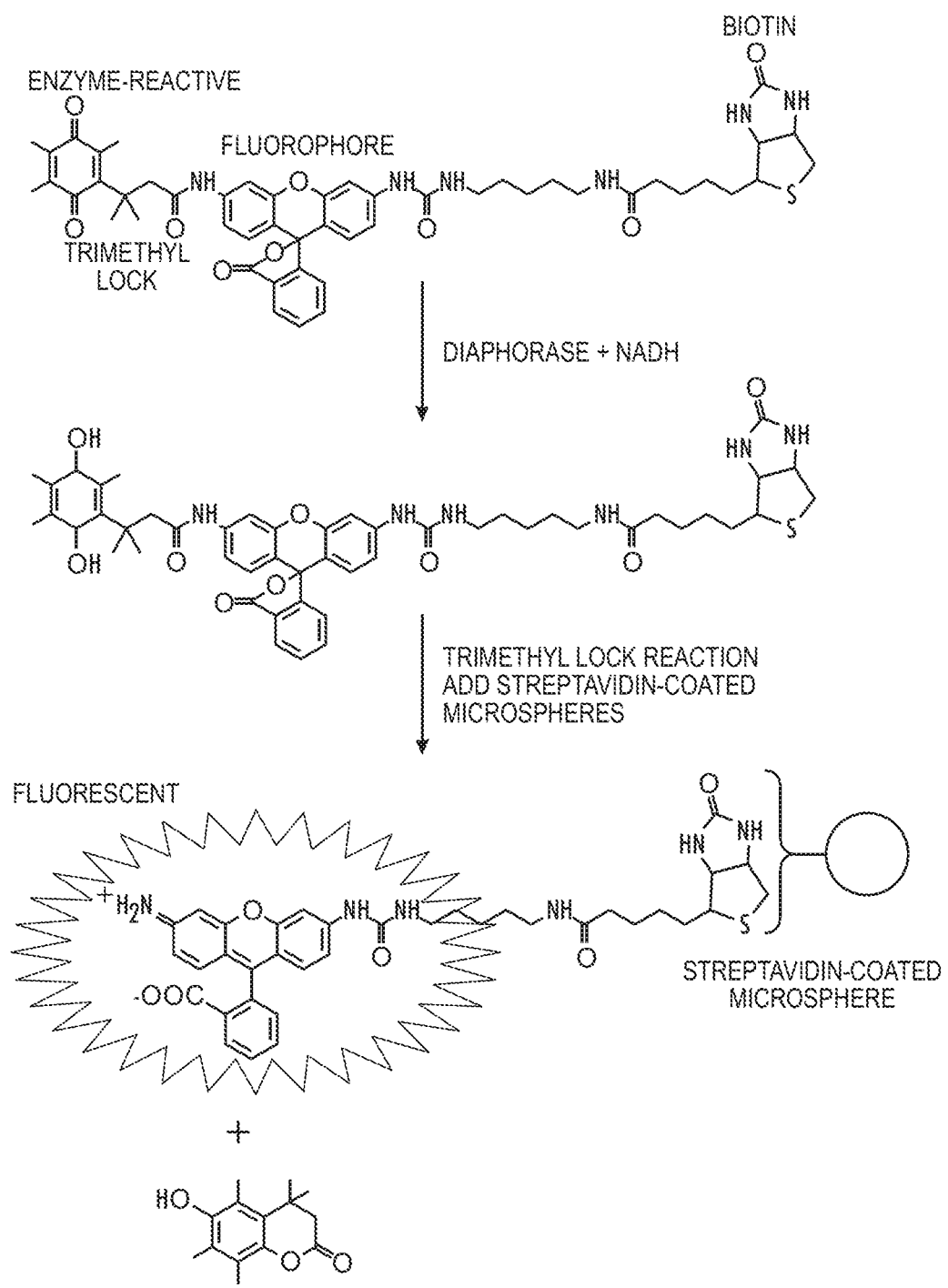
FIG. 8 is an exemplary reaction schematic showing a latent fluorescent biotin-containing compound revealed by a trimethyl lock reaction and subsequently linked to a streptavidin-coated microsphere, according to an embodiment of the disclosure.

In certain embodiments, the latent fluorophore including a suitable linking group, for example biotin, can be used in solution and bound to the microsphere coated with a suitable functional group, for example streptavidin, after the enzyme assay is performed. FIG. 8 is a reaction schematic showing an exemplary embodiment of a latent fluorescent compound revealed by a trimethyl lock reaction and subsequently linked to a streptavidin-coated microsphere. The enzyme assay is performed as described above using latent fluorophores including a biotin group. Streptavidin-coated microspheres are subsequently introduced into the test sample and reference sample. The biotin binds to the streptavidin, which connects the fluorophore to the microsphere. The microsphere can then be used to isolate the fluorophore from the samples as described above.

In further exemplary embodiments according to the disclosure, a multiplex array can be used to examine the activity of multiple enzymes at the same time by using different enzyme-reactive quenching groups and a different fluorophore for each enzymatic reaction. The fluorescence of the different fluorophores connected to different microspheres can be analyzed using flow cytometry or spatially modulated fluorescence detection technology. Suitable enzymes include, but are not limited to, proteases, phosphatases, and dehydrogenases.

Figure 9A:
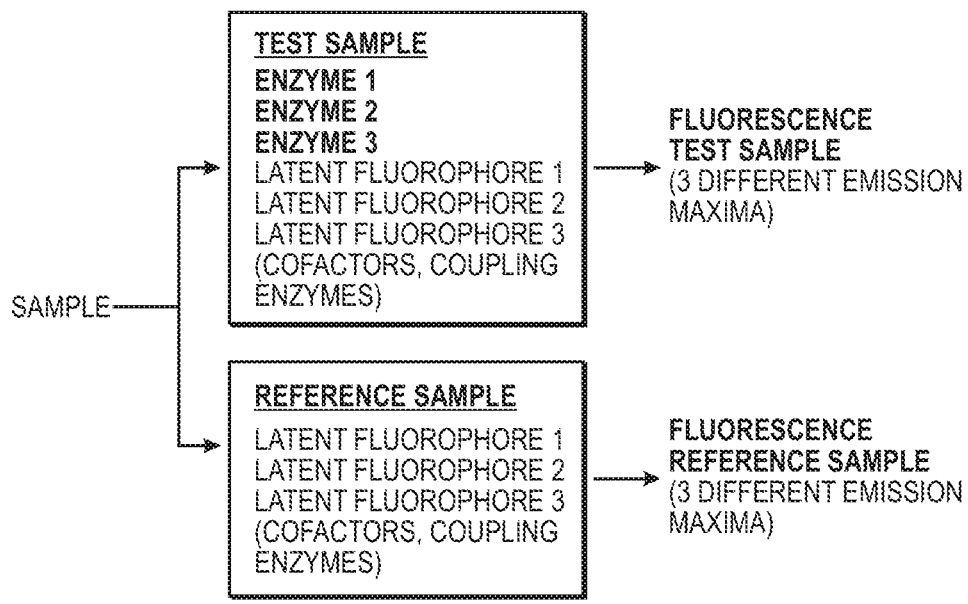
FIG. 9A is a flowchart showing the steps for a general enzymatic multiplexed differential assay using fluorophores having different emission properties, according to an exemplary embodiment of the disclosure.

FIG. 9A is a flowchart showing the steps for a general enzymatic multiplexed differential assay of a sample using fluorophores having different emission properties, according to an exemplary embodiment of the disclosure. Although three different enzymes are used in the exemplary embodiment shown in FIG. 9A, a greater or fewer number of enzymes may be used. The sample is divided between a test sample and a reference sample. The test sample contains three different enzymes, three different latent fluorophores, plus any necessary cofactors and coupling enzymes, for example diaphorase. The reference sample contains all of the components in the test sample except for the three different enzymes. The three different fluorophores have different enzyme-reactive quenching groups and different emission properties, for example maxima. The fluorescence signals from the test sample and the reference sample are measured, and the fluorescence signals of the reference sample are subtracted from those of the test sample to yield differential measurements. In certain embodiments, the microspheres are magnetic.

Figure 9B:
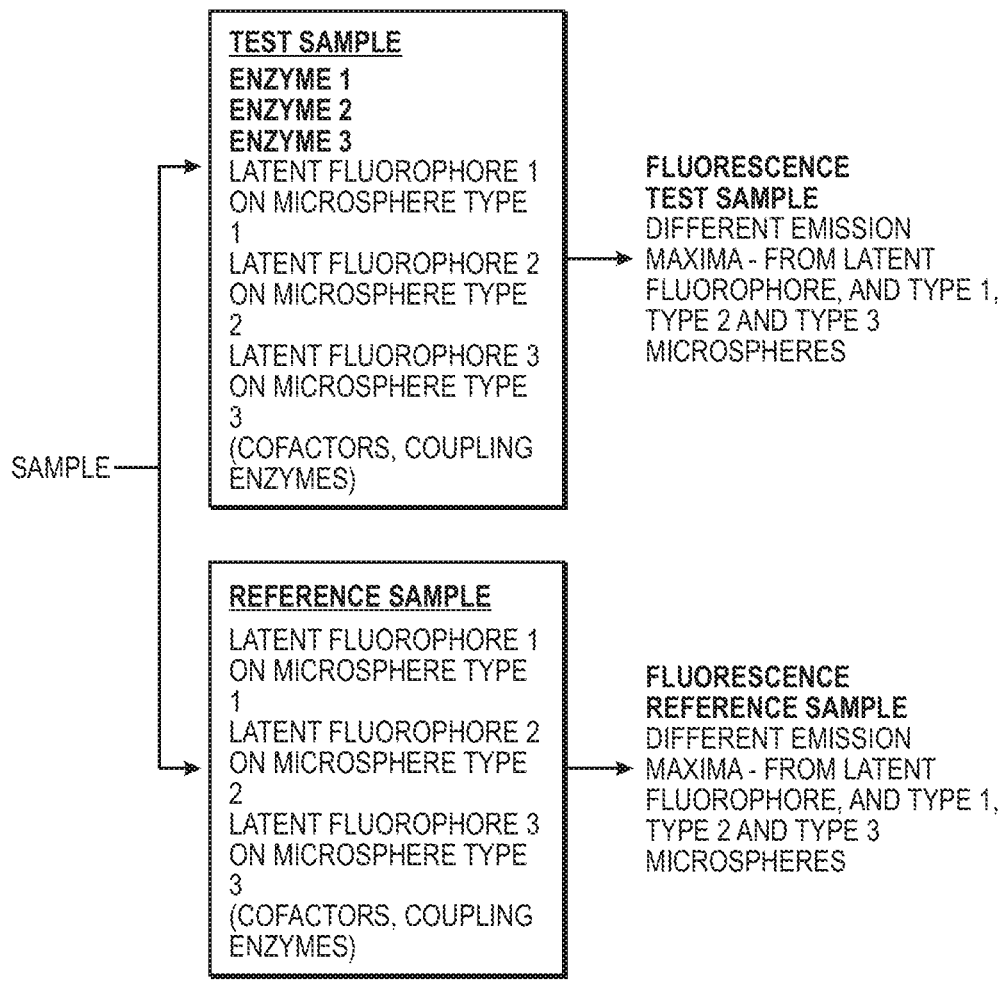
FIG. 9B is a flowchart showing the steps for an enzymatic multiplexed differential assay using fluorescent microspheres having different emission properties, according to an exemplary embodiment of the disclosure.

FIG. 9B is a flowchart showing the steps for a general enzymatic multiplexed differential assay of a sample using fluorescent microspheres having different emission properties according to an exemplary embodiment of the disclosure. Although three different enzymes are used in the exemplary embodiment shown in FIG. 9B, a greater or fewer number of enzymes may be used. The sample is divided between a test sample and a reference sample. The test sample contains three different enzymes, three different latent fluorophores, plus any necessary cofactors and coupling enzymes, for example diaphorase. The reference sample contains all of the components in the test sample except for the three different enzymes. The three different fluorophores have different enzyme-reactive quenching groups and the same emission properties. Each of the three different latent fluorophores is coupled to a microsphere having a specific fluorescent property, i.e., latent fluorophore 1 is coupled to microsphere type 1, latent fluorophore 2 is coupled to microsphere type 2, and latent fluorophore 3 is coupled to microsphere type 3, where microsphere types 1-3 have different fluorescent properties, for example emission maxima. Although the three latent fluorophores have the same fluorescence properties, the activity of the three different enzymes may be monitored by separating the microbeads having specific fluorescent properties, for example by flow cytometry. The fluorescence signals from the fluorophores and/or microspheres of the test sample and the reference sample are measured, and the fluorescence signals of the reference sample are subtracted from those of the test sample to yield differential measurements. In another embodiment, the three latent fluorophores have different emission properties. In certain embodiments, all or some of the microspheres are magnetic.

Figure 9C:
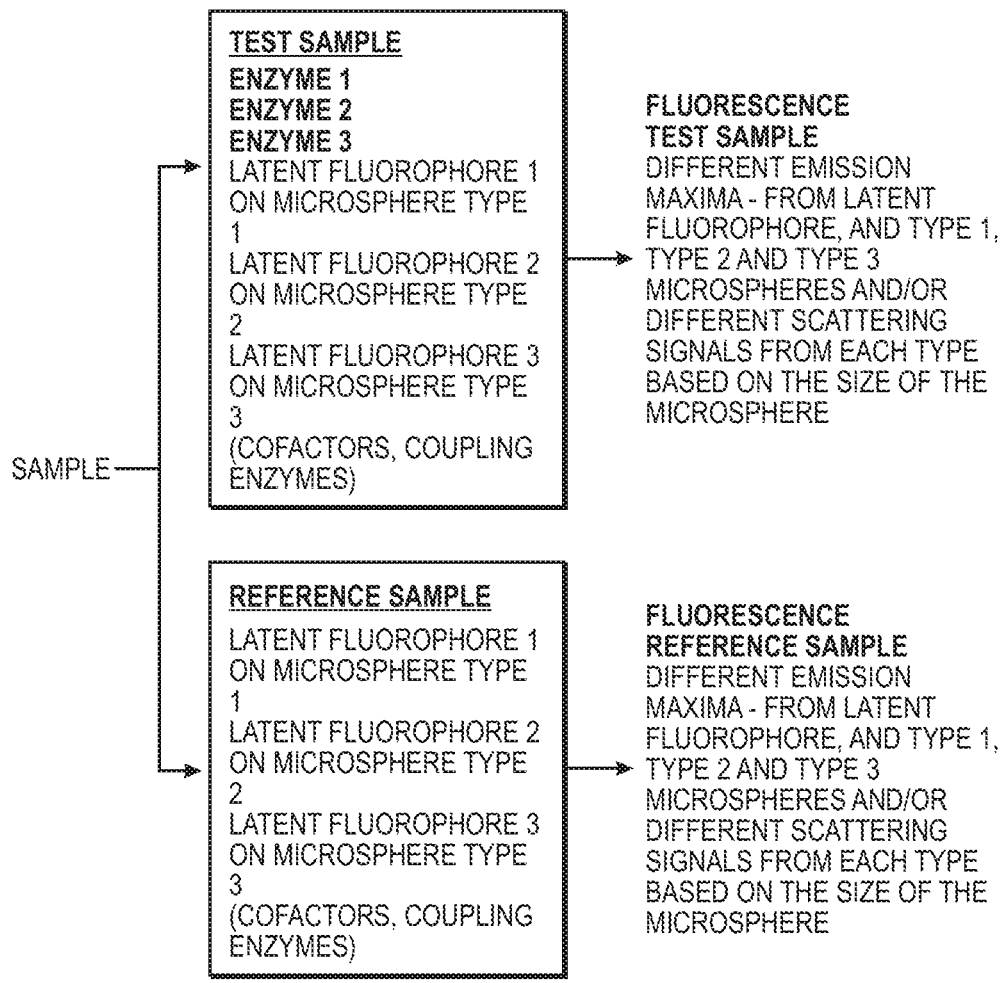
FIG. 9C is a flowchart showing the steps for an enzymatic multiplexed differential assay using fluorescent microspheres having different sizes, according to an exemplary embodiment of the disclosure.

FIG. 9C is a flowchart showing the steps for a general enzymatic multiplexed differential assay of a sample using fluorescent microspheres having different sizes, according to an exemplary embodiment of the disclosure. Although three different enzymes are used in the exemplary embodiment shown in FIG. 9C, a greater or fewer number of enzymes may be used. The sample is divided between a test sample and a reference sample. The test sample contains three different enzymes, three different latent fluorophores, plus any necessary cofactors and coupling enzymes, for example diaphorase. The reference sample contains all of the components in the test sample except for the three different enzymes. The three different fluorophores have different enzyme-reactive quenching groups and the same emission properties. Each of the three different latent fluorophores is coupled to a microsphere having a specific particle size, i.e., latent fluorophore 1 is coupled to microsphere type 1, latent fluorophore 2 is coupled to microsphere type 2, and latent fluorophore 3 is coupled to microsphere type 3, where microsphere types 1-3 have different sizes. The microspheres may be magnetic and/or fluorescent, with the same or different fluorescent properties. The difference in particle sizes between the different microspheres causes different scattering signals from each size of microsphere. Although the three latent fluorophores have the same fluorescence properties, the activity of the three different enzymes may be monitored by distinguishing the microspheres by size based on the different scattering properties, for example using flow cytometry. The fluorescence signals and scattering signals from the fluorophores and/or microspheres of the test sample and the reference sample are measured, and the fluorescence signals of the reference sample are subtracted from those of the test sample to yield differential measurements. In another embodiment, the three latent fluorophores have different emission properties.

In at least certain exemplary embodiments, the enzymatic multiplexed differential assays shown in FIGS. 9A-9C may be applied to simultaneously screen compounds on multiple enzyme targets in a multiplexed differential screening assay. For example, a multiplexed differential screening assay may be used to determine which, if any, of a number of enzymes shows activity in the presence of a test compound.

Figure 10A:
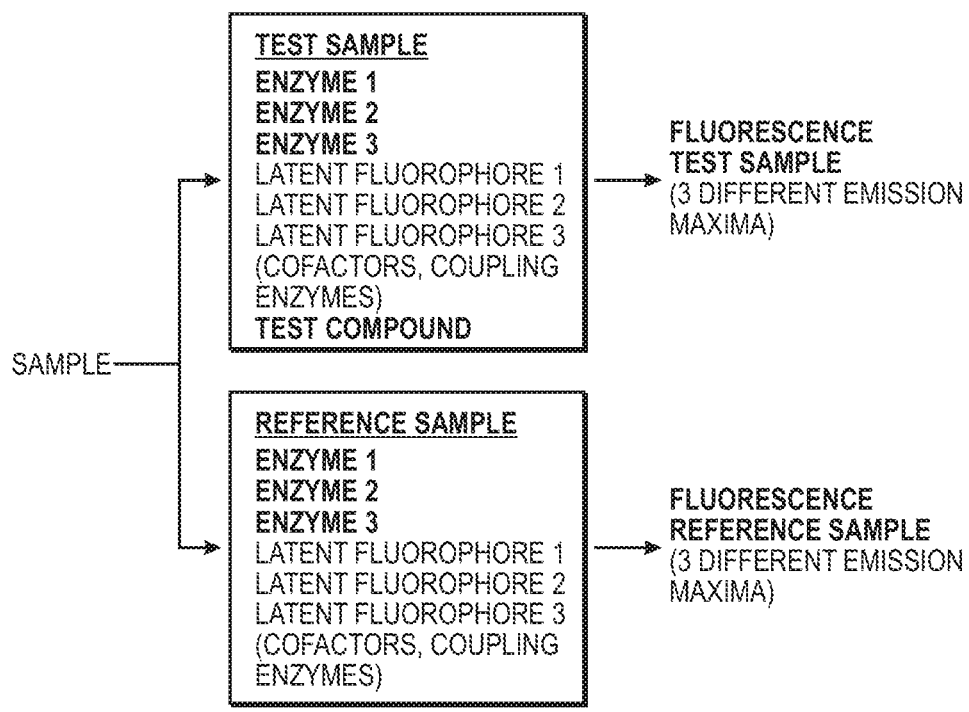
FIG. 10A is a flowchart showing the steps for a general enzymatic multiplexed differential screening assay using fluorophores having different emission properties, according to an exemplary embodiment of the disclosure.
Figure 10B:
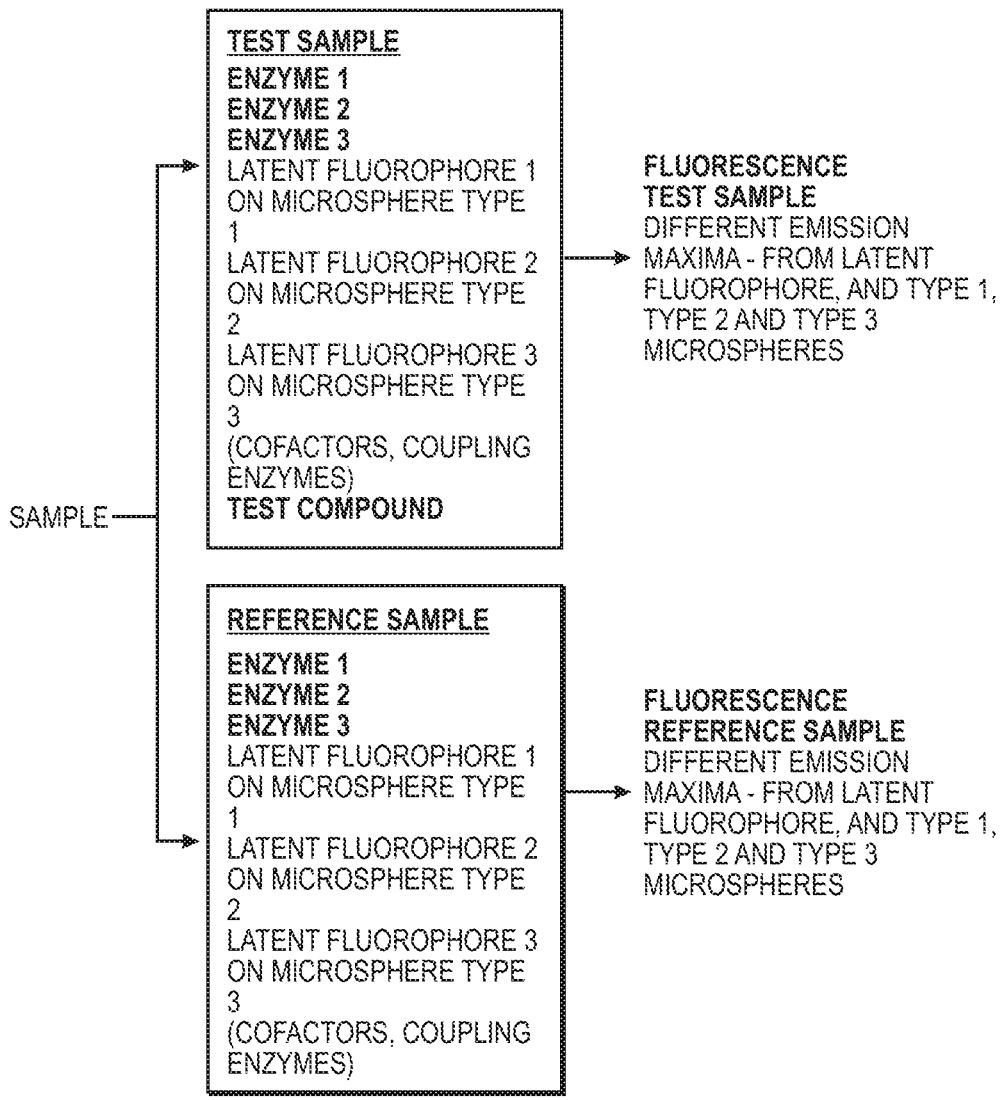
FIG. 10B is a flowchart showing the steps for a general enzymatic multiplexed differential screening assay using fluorescent microspheres having different emission properties, according to an exemplary embodiment of the disclosure.

FIG. 10A is a flowchart showing the steps for a general enzymatic multiplexed differential screening assay of a sample using fluorophores having different emission properties, according to an exemplary embodiment of the disclosure. Although three different enzymes are used in the exemplary embodiment shown in FIG. 10A, a greater or fewer number of enzymes may be used. The sample is divided between a test sample and a reference sample. The test sample contains three different enzymes, three different latent fluorophores, a test compound, plus any necessary cofactors and coupling enzymes, for example diaphorase. The reference sample contains all of the components in the test sample except for the test compound. The three different fluorophores have different enzyme-reactive quenching groups and different emission properties, for example maxima. Although the three latent fluorophores have the same fluorescence properties, the activity of the three different enzymes may be monitored by separating the microbeads having specific fluorescent properties, for example by flow cytometry. The fluorescence signals from the test sample and the reference sample are measured, and the fluorescence signals of the reference sample are subtracted from those of the test sample to yield differential measurements. In certain embodiments, the microspheres are magnetic FIG. 10B is a flowchart showing the steps for a general enzymatic multiplexed differential screening assay of a sample using fluorescent microspheres having different emission properties, according to an exemplary embodiment of the disclosure. Although three different enzymes are used in the exemplary embodiment shown in FIG. 10B, a greater or fewer number of enzymes may be used. The sample is divided between a test sample and a reference sample. The test sample contains three different enzymes, three different latent fluorophores, a test compound, plus any necessary cofactors and coupling enzymes, for example diaphorase. The reference sample contains all of the components in the test sample except for the test compound. The three different fluorophores have different enzyme-reactive quenching groups and the same emission properties. Each of the three different latent fluorophores is coupled to a microsphere having a specific fluorescent property, i.e., latent fluorophore 1 is coupled to microsphere type 1, latent fluorophore 2 is coupled to microsphere type 2, and latent fluorophore 3 is coupled to microsphere type 3, where microsphere types 1-3 have different fluorescent properties, for example emission maxima. Although the three latent fluorophores have the same fluorescence properties, the activity of the three different enzymes may be monitored by separating the microbeads having specific fluorescent properties, for example by flow cytometry. The fluorescence signals from the fluorophores and/or microspheres of the test sample and the reference sample are measured, and the fluorescence signals of the reference sample are subtracted from those of the test sample to yield differential measurements. In another embodiment, the three latent fluorophores have different emission properties. In certain embodiments, all or some of the microspheres are magnetic.

Figure 10C:
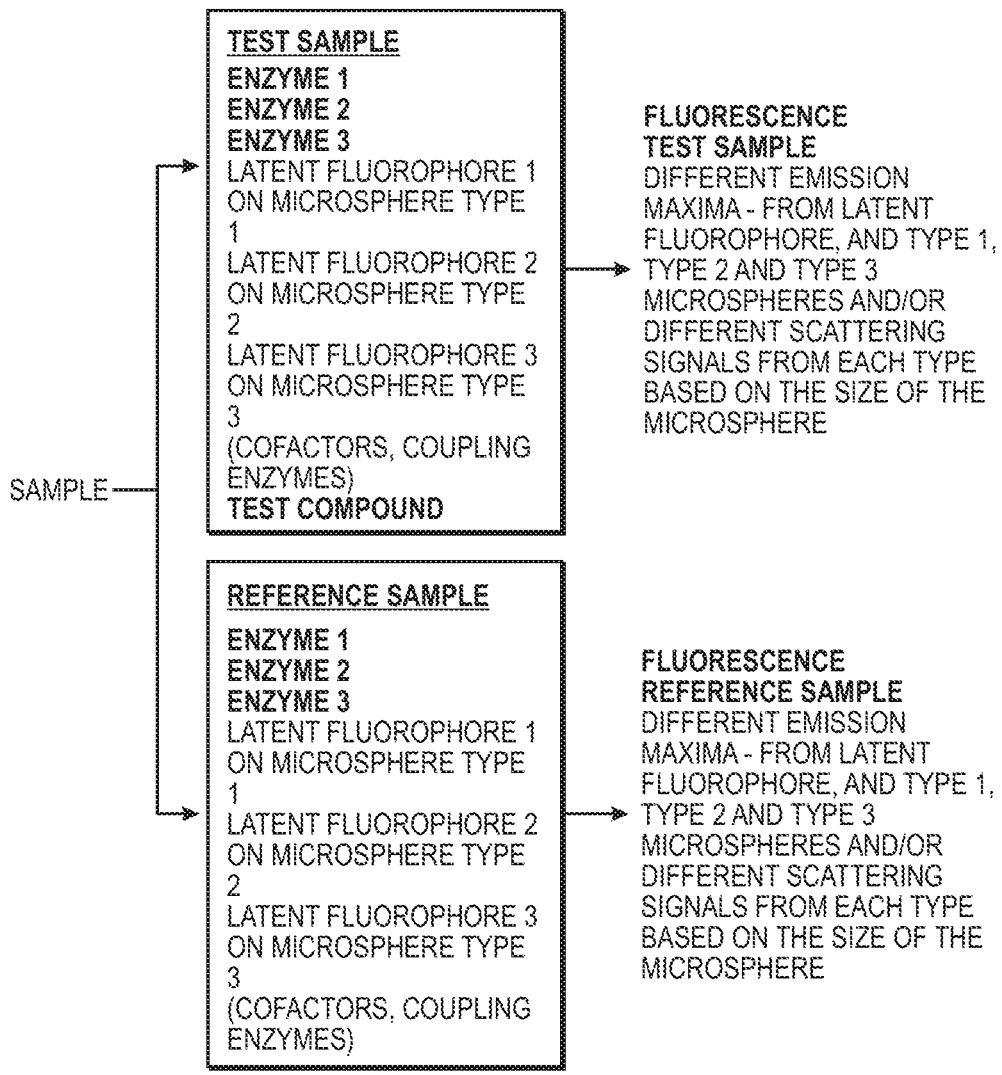
FIG. 10C is a flowchart showing the steps for a general enzymatic multiplexed differential screening assay using fluorescent microspheres having different sizes, according to an exemplary embodiment of the disclosure.

FIG. 10C is a flowchart showing the steps for a general enzymatic multiplexed differential screening assay of a sample using fluorescent microspheres having different particle sizes, according to an exemplary embodiment of the disclosure. Although three different enzymes are used in the exemplary embodiment shown in FIG. 10C, a greater or fewer number of enzymes may be used. The sample is divided between a test sample and a reference sample. The test sample contains three different enzymes, three different latent fluorophores, a test compound, plus any necessary cofactors and coupling enzymes, for example diaphorase. The reference sample contains all of the components in the test sample except for the test compound. The three different fluorophores have different enzyme-reactive quenching groups and the same emission properties. Each of the three different latent fluorophores is coupled to a microsphere having a specific particle size, i.e., latent fluorophore 1 is coupled to microsphere type 1, latent fluorophore 2 is coupled to microsphere type 2, and latent fluorophore 3 is coupled to microsphere type 3, where microsphere types 1-3 have different sizes. The microspheres may be magnetic and/or fluorescent, with the same or different fluorescent properties. The difference in particle sizes between the different microspheres causes different scattering signals from each size of microsphere. Although the three latent fluorophores have the same fluorescence properties, the activity of the three different enzymes may be monitored by distinguishing the microspheres by size based on the different scattering properties, for example during flow cytometry. The fluorescence signals from the fluorophores and/or microspheres of the test sample and the reference sample are measured, and the fluorescence signals of the reference sample are subtracted from those of the test sample to yield differential measurements. In another embodiment, the three latent fluorophores have different emission properties. In certain embodiments, all or some of the microspheres are magnetic.

Further exemplary embodiments of the disclosure relates to kits comprising a composition, where the composition comprises at least one latent fluorophore comprising at least one enzyme-reactive quenching group and at least one conjugative group, and at least one support connectible to the at least one latent fluorophore via at least one conjugative group, as described herein. These kits may include, for example, at-home testing kits for analyzing phenylalanine levels in blood.

As used herein, the terms "a", "an", and "the" are intended to encompass the plural as well as the singular. In other words, for ease of reference only, the terms "a" or "an" or "the" may be used herein, such as "a support", "an enzyme", "the microsphere", etc., but are intended, unless explicitly indicated to the contrary, to mean "at least one," such as "at least one support", "at least one enzyme", "the at least one microsphere", etc. This is true even if the term "at least one" is used in one instance, and "a" or "an" or "the" is used in another instance, e.g. in the same paragraph or section. Furthermore, as used herein, the phrase "at least one" means one or more, and thus includes individual components as well as mixtures/combinations.

The term "comprising" (and its grammatical variations) as used herein is used in the inclusive sense of "having" or "including," with which it may be used interchangeably. These terms are not to be construed as being used in the exclusive sense of "consisting only of" unless explicitly so stated.

Other than where expressly indicated, all numbers expressing quantities of ingredients and/or reaction conditions are to be understood as being modified in all instances by the term "about." This includes terms such as "all" or "none" and variants thereof. As used herein, the modifier "about" means within the limits that one of skill in the art would expect with regard to the particular quantity defined; this may be, for example, in various embodiments, ±10% of the indicated number, ±5% of the indicated number, ±2% of the indicated number, ±1% of the indicated number, ±0.5% of the indicated number, or ±0.1% of the indicated number.

Additionally, where ranges are given, it is understood that the endpoints of the range define additional embodiments, and that subranges including those not expressly recited are also intended to include additional embodiments.

As used herein, "formed from," "generated by," and variations thereof, mean obtained from chemical reaction of, wherein "chemical reaction," includes spontaneous chemical reactions and induced chemical reactions. As used herein, the phrases "formed from" and "generated by" are open ended and do not limit the components of the composition to those listed.

The compositions and methods according to the present disclosure can comprise, consist of, or consist essentially of the elements and limitations described herein, as well as any additional or optional ingredients, components, or limitations described herein or otherwise known in the art.

It should be understood that, unless explicitly stated otherwise, the steps of various methods described herein may be performed in any order, and not all steps must be performed, yet the methods are still intended to be within the scope of the disclosure.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method of detecting and/or measuring the concentration of an analyte in a sample, the method comprising:
    a. providing a composition comprising:
        i. at least one latent fluorophore comprising at least one enzyme-reactive quenching group and at least one conjugative group, and
        ii. at least one support connectable to the at least one latent fluorophore by the at least one conjugative group;
    b. providing a test sample and a reference sample;
    c. providing at least one first unquenching enzyme capable of releasing the enzyme-reactive quenching group from the at least one latent fluorophore, and at least one second enzyme capable of reacting with at least one analyte;
    d. contacting the test sample with the composition, the at least one first unquenching enzyme, and the at least one second enzyme, and detecting any fluorescence signal using spatially modulated fluorescence detection; and
    e. contacting the reference sample with the composition and the at least one first unquenching enzyme, and detecting any fluorescence signal using spatially modulated fluorescence detection,
    wherein the at least one latent fluorophore is chosen from trimethyl lock fluorophores, wherein the trimethyl lock fluorophore is chosen from compounds of Chemical Formula 1, Chemical Formula 2, Chemical Formula 3, or combinations thereof:

Chemical Formula 1

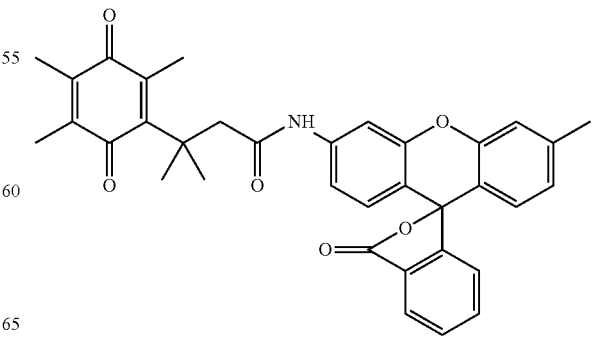

29
-continued

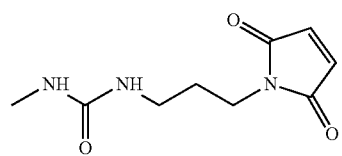

Chemical Formula 2

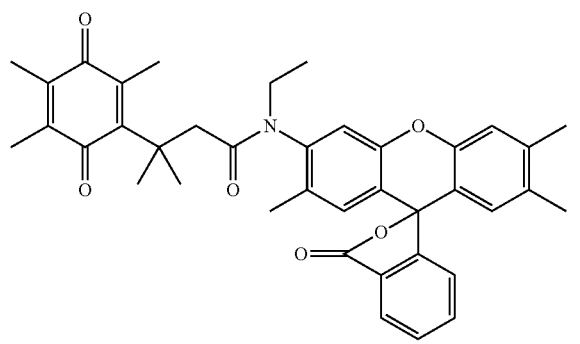

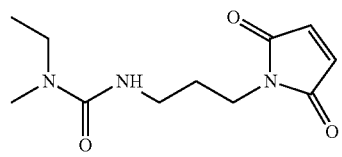

30
-continued

Chemical Formula 3

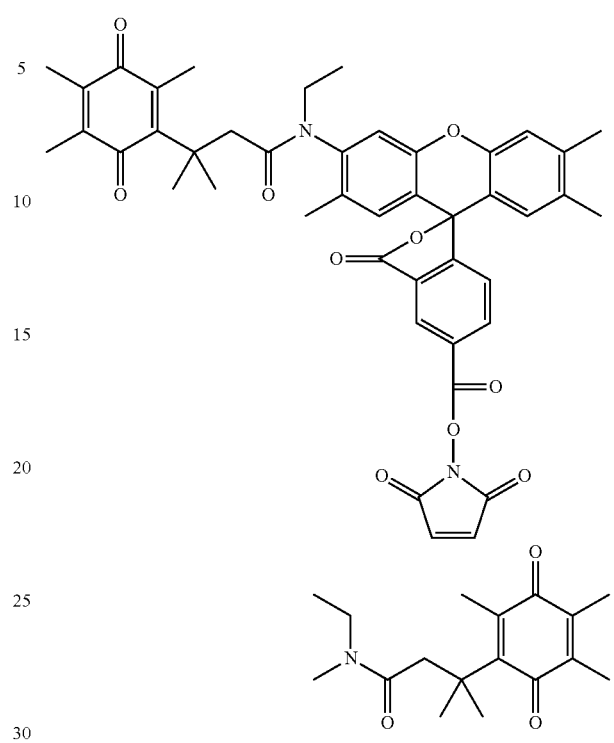

2. The method of claim 1, further comprising:
f. measuring the fluorescence signal of the test sample and the fluorescence signal of the reference sample.
3. The method of claim 2, further comprising:
g. comparing the fluorescence signal of the test sample with the fluorescence signal of the reference sample.
4. The method of claim 1, wherein the at least one support is chosen from microspheres.
5. The method of claim 4, wherein the at least one support is magnetic.
6. The method of claim 1, wherein the analyte is phenylalanine, the at least one first unquenching enzyme is diaphorase, and the at least one second enzyme is phenylalanine dehydrogenase.
7. The method of claim 6, wherein the sample is blood.
8. The method of claim 1, wherein the sample is blood.

* * * * *